US012593767B2

(12) United States Patent
Tricoli

(10) Patent No.: US 12,593,767 B2
(45) Date of Patent: Apr. 7, 2026

(54) PROTOPLAST ISOLATION AND REGENERATION OF PLANTS

(71) Applicant: The Regents of the University of California, Oakland, CA (US)

(72) Inventor: David Tricoli, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/726,884

(22) Filed: Apr. 22, 2022

(65) Prior Publication Data

US 2022/0248621 A1 Aug. 11, 2022

Related U.S. Application Data

(63) Continuation of application No. PCT/US2020/057157, filed on Oct. 23, 2020.

(60) Provisional application No. 62/925,148, filed on Oct. 23, 2019.

(51) Int. Cl.
*A01H 4/00* (2006.01)
*A01H 6/88* (2018.01)

(52) U.S. Cl.
CPC .................. *A01H 4/00* (2013.01); *A01H 6/88* (2018.05)

(58) Field of Classification Search
None
See application file for complete search history.

(56) References Cited

U.S. PATENT DOCUMENTS

2002/0173037 A1* 11/2002 Pati ........................ A01H 4/002
435/430.1

OTHER PUBLICATIONS

Trocoli, Grape protoplast isolation and regeneration of plants for use in gene editing technology. Renewal Progress Report for CDFA Agreement Number #18-0397. (Year: 2020).*

Tricoli_2019_Created date (Year: 2019).*
Bertini et al (Regeneration of plants from embryogenic callus-derived protoplasts of Garganega and Sangiovese grapevine (*Vitis vinifera* L.) cultivars. Plant Cell, Tissue and Organ Culture. 138:239-246, May 2019) (Year: 2019).*
Mii et al (High-frequency callus formation from protoplasts of Vitis labruscana Bailey and Vitis thunbergia Sieb. et Zucc. by embedding in gellan gum. Scientia Horticulturae, 46, 253-260, 1991) (Year: 1991).*
Trocoli, Grape protoplast isolation and regeneration of plants for use in gene editing technology. Renewal Progress Report for CDFA Agreement No. #18-0397 (Year: 2020).*
Tricoli et al (Culture of soybean mesophyll protoplasts in alginate beads. Plant Cell Reports, 5: p. 334-337, 1986) (Year: 1986).*
Altman et al (Stabilization of Oat Leaf Protoplasts through Polyamine mediated Inhibition of Senescence. Plant Physiol. 60, 570-574, 1977), (Year: 1977).*
Zhu et al (Highly efficient system of plant regeneration from protoplasts of grapevine (*Vitis vinzfera* L.) through somatic embryogenesis by using embryogenic callus culture and activated charcoal. Plant Science 123, 151-157, 1997) (Year: 1997).*
Ui et al (Cooperative Effect of Activated Charcoal and Gellan Gum on Grape Protoplast Culture. Agric. Biol. Chem., 54 (1), 207-209, 1990). (Year: 1990).*
Malnoy et al (DNA-Free Genetically Edited Grapevine and Apple Protoplast Using CRISPR/Cas9 Ribonucleoproteins. Frontiers in plant science. 1-9, 2016). (Year: 2016).*
Akula (In Vitro Plant Regeneration and Genetic Transformation Studies in Grapevine: Crimson Seedless. Ph.D. Thesis, 2007). (Year: 2007).*
International Search Report and Written Opinion in PCT/US2020/057157 mailed Feb. 4, 2021; 8 pages.
Tricoli, "Grape Protoplast Isolation and regeneration of plants for use in gene editing technology"; Renewal Progress Report for CDFA Agreement No. #18-0397; https://static.cdfa.ca.gov/PiercesDisease/reports%2F2019%2FTricoli%20Renewal%20Report%202%2022%202019.pdf as accessed on the internet Dec. 18, 2020; Feb. 20, 2019. 10 pages.

* cited by examiner

*Primary Examiner* — Wayne Zhong
(74) *Attorney, Agent, or Firm* — Kilpatrick Townsend & Stockton LLP

(57) ABSTRACT

The present disclosure provides methods for inducing callus formation and plant regeneration from isolated protoplasts of grape. This technology allows for the production of non-chimeric gene edits in grape plants by allowing the delivery of DNA through the plant cell membrane with the recovery of whole plants from a single edited cell.

19 Claims, 21 Drawing Sheets

PROTOPLAST ISOLATION AND REGENERATION OF PLANTS

CROSS-REFERENCES TO RELATED APPLICATIONS

The present application is a bypass continuation of International Application PCT/US2020/057157, filed Oct. 23, 2020, which claims priority to U.S. Provisional Application No. 62/925,148, filed on Oct. 23, 2019, each of which is incorporated herein by reference in its entirety.

BACKGROUND OF THE INVENTION

The CRISPR-Cas9 gene editing technology allows for precise alterations in plant genomes. Given the revolution occurring in gene-editing technology, protoplast culture provides one of the best avenues for producing non-chimeric gene edited plants for clonally propagated species. Although non-protoplast-based gene editing techniques are being developed for many crops, recovery of non-chimeric gene-edited plants is still problematic. In seed propagated crops, gene-editing technology can be introduced via *Agrobacterium tumefaciens* or biolistic-mediated DNA delivery systems. Once gene editing has been accomplished, the CRISPR-Cas9 insert can be segregated out of the population in the next generation with the null segregant, containing only the desired gene edit and advanced using traditional plant breeding. However, for clonally propagated plants like wine grapes, it is not possible to use breeding to eliminate the CRISPR-Cas9 insert and still maintain the fidelity of the clonal germplasm.

A limited number of grapevine clones have been used for many decades to produce high quality wine. These clones are maintained by vegetative propagation to preserve the intrinsic quality of this material. Therefore, the implementation of genome editing technology to introduce new traits into existing *Vitis* cultivars without altering their essential characters and identity is crucial.

Protoplast culture provides one of the best avenues for producing non-chimeric gene edited plants for clonally propagated species. CRISPR-Cas9 has been introduced into plants protoplasts using PEG or electroporation and expressed transiently without integration of the CRISPR-Cas9 DNA. Cell walls re-form on the protoplast in 48 to 72 hours and the edited cells can be stimulated to form mini callus colonies. However regenerated of whole plants from protoplasts has not previously been achieved in grape.

There is thus a need for new methods for introducing genetic modifications into protoplasts from clonally propagated plants such as grape plants, and for regenerating plants from the modified protoplasts. The present disclosure satisfies this need and provides other advantages as well.

BRIEF SUMMARY OF THE INVENTION

In one aspect, the present disclosure provides a method of regenerating a grape plant from a grape protoplast, the method comprising (i) encapsulating an isolated grape protoplast in a gel matrix; (ii) culturing the encapsulated protoplast in the presence of an osmotically conditioned grape cell suspension culture or osmotically adjusted conditioned medium, wherein the protoplast undergoes cell division; (iii) culturing the encapsulated protoplast in the presence of one or more antioxidants or polyamines or both, wherein the protoplast undergoes cell division and forms a callus colony; (iv) transferring the callus colony to an agar-solidified feeder medium, wherein the callus colony develops into a somatic embryo; and (v) transferring the somatic embryo to an agar-solidified plant medium, wherein the somatic embryo undergoes germination.

In some embodiments of the method, the gel matrix is an alginate bead. In some embodiments, step (iii) is performed in the presence of one or more antioxidants and one or more polyamines. In some embodiments, the one or more antioxidants are selected from the group consisting of ascorbic acid, citric acid, reduced glutathione, and L-cysteine. In some embodiments, the one or more antioxidants comprise ascorbic acid, citric acid, reduced glutathione, and L-cysteine. In some embodiments, the polyamine is spermine. In some embodiments, the encapsulated protoplast is cultured in step (iii) in a feeder cell suspension. In some embodiments, the method further comprises a step in which the alginate bead formed in step (i) is dissolved prior to the transferring of step (v). In some embodiments, the alginate bead formed in step (i) is not dissolved prior to the transferring of step (v).

In some embodiments, the method further comprises a step in which the protoplast is isolated from an embryonic callus or somatic embryo prior to step (i). In some embodiments, the embryonic callus or somatic embryo from which the protoplast is isolated is derived from an anther filament. In some embodiments, the protoplast is isolated from an embryonic callus or somatic embryo culture. In some embodiments, the embryonic callus or somatic embryo culture is produced by generating a suspension culture from an anther-derived callus and plating aliquots of the suspension culture onto callus or somatic embryo induction medium.

In some embodiments, the method further comprises a step in which a guide RNA and an RNA-guided nuclease are introduced into the isolated protoplast prior to the encapsulating of step (i). In some embodiments, the RNA-guided nuclease is a Cas protein. In some embodiments, the Cas protein is selected from the group consisting of Cas3, Cas5, Cas6, Cas7, Cas8, Cas9, Cas10, Cas12, Cpf1, Cas13, Cse1, Cse2, Csy1, Csy2, Csy3, GSU0054, Csm2, Cmr5, Csx11, Csx10, Csf1, Csn2, Cas4, C2c1, C2c3, and C2c2. In some embodiments, the RNA-guided nuclease is Cas9 or Cpf1. In some embodiments, the RNA-guided nuclease is Cas9. In some embodiments, the guide RNA and RNA-guided nuclease are introduced into the protoplast using PEG or electroporation. In some embodiments, the guide RNA and RNA-guided nuclease are introduced by introducing one or more polynucleotides encoding the guide RNA and the RNA-guided nuclease into the protoplast. In some embodiments, the guide RNA and RNA-guided nuclease are introduced by introducing a ribonucleoprotein particle comprising the guide RNA and the nuclease into the protoplast. In some embodiments, the one or more polynucleotides encoding the guide RNA and the RNA-guided nuclease are DNA. In some embodiments, the one or more polynucleotides do not integrate into the protoplast genome. In some embodiments, the guide RNA and the RNA-guided nuclease are transiently expressed in the protoplast. In some embodiments, the guide RNA and RNA-guided nuclease induce an alteration in the protoplast genome. In some embodiments, the grape plant is a table grape, wine grape, or grape rootstock. In some embodiments, the method further comprises a step wherein the somatic embryo developed in step (iv) is stored indefinitely on sorbitol-containing medium prior to the transferring to the plant medium of step (v), wherein the plant medium does not comprise sorbitol.

In another aspect, the present disclosure provides genetically modified protoplasts generated using any of the herein-disclosed methods, as well as calli, embryos, and plants derived from the genetically modified protoplasts.

Other objects, features, and advantages of the present invention will be apparent to one of skill in the art from the following detailed description and figures.

DETAILED DESCRIPTION OF THE INVENTION

1. Introduction

Figure 1:
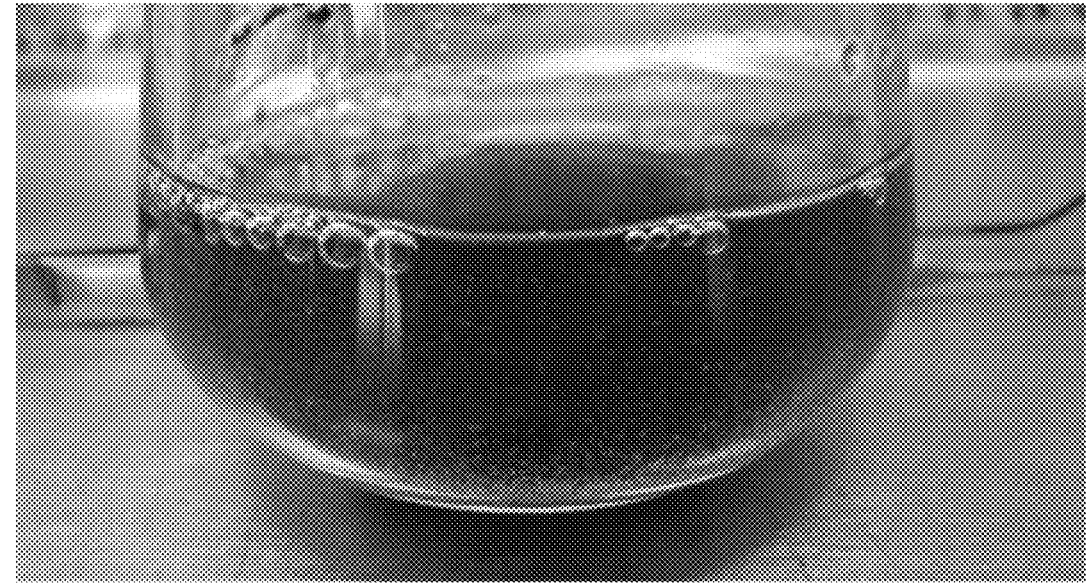
FIG. 1. Fine suspension cultures of 1103P growing in WPM, 20 g/l sucrose, 1 g/l casein, 1 mM MES, 1,000 mg/l activated charcoal, 10 mg/l picloram, 2 mg/l meta-topolin, 100 mg/l ascorbic acid and 120 mg/l reduced glutathione (Pic/MTag).

The present disclosure provides methods for inducing callus formation and plant regeneration from isolated protoplasts of grape. This technology allows for the production of non-chimeric gene edits in grape plants by allowing the delivery of DNA through the plant cell membrane with the recovery of whole plants from a single edited cell.

The present methods involve one or more of a series of steps for effecting the modification and regeneration of grape plants, including: (i) the isolation of protoplasts; (ii) the modification of isolated protoplasts using RNA-guided nucleases such as CRISPR-Cas9; (iii) the encapsulation of isolated protoplasts in a gel matrix such as alginate beads; (iv) the culturing of encapsulated protoplasts under conditions in which they divide and form a callus; (v) the formation of a somatic embryo from the callus; and (vi) the germination of the embryo to form a plant.

Using the present methods, it is possible to make precise genomic alterations in clonally propagated plants such as grape. The present methods can be used with any type of grape plant, including table grapes, wine grapes, or grape rootstock. Grapes can be used from any variety of *Vitis vinifera, Vitis labrusca, Vitis riparia, Vitis rotundifolia, Vitis rupestris, Vitis aestivalis,* or *Vitis mustangensis.* Single species and hybrids can be used. A non-limiting list of table grapes that can be used include any white, green, red, blue, or black grapes, e.g., Perlette, Sugraone, Thompson Seedless, Niagara, Calmeria, Italia, Autumn King, Princess, Cotton Candy, Flame Seedless, Swenson Red, Yates, Red Globe, Ruby Seedless, Christmas Rose, Emperor, Rouge, Crimson Seedless, Tudor Premium Red, Scarlet Royal, Cardinal, Koshu, Delaware, Ruby Roman, Vintage Red, Muscato, Beauty Seedless, Concord, Thomcord, Muscat Hamburg, Autumn Royal, Fantasy Seedless, Marroo, Niabell, Summer Royal, Kyoho, Pione, and St. Theresa. A non-limiting list of wine grapes that can be used include red, white, and rose grapes, e.g., Cabernet Franc, Cabernet Sauvignon, Carmenere, Chardonnay, Gewurztraminer, Grenache, Malbec, Merlot, Muscat Ottonel, Nebbiolo, Pinotage, Pinot Grigio/Gris, Pinot Noir, Riesling, Sauvignon Blanc, Semillon, Shiraz/Syrah, Tempranillo, Viognier, and Zinfandel. In particular embodiments, the grapes are Chardonnay, Thompson seedless, Merlot, or the grape rootstock 1103P or 101-14.

The present disclosure also provides protoplasts, e.g., isolated and/or genetically modified protoplasts, produced using the herein-described methods, as well as calli, embryos, and plants generated from the protoplasts.

2. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.8X, 0.81X, 0.82X, 0.83X, 0.84X, 0.85X, 0.86X, 0.87X, 0.88X, 0.89X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, 1.1X, 1.11X, 1.12X, 1.13X, 1.14X, 1.15X, 1.16X, 1.17X, 1.18X, 1.19X, and 1.2X. Thus, "about X" is intended to teach and provide written description support for a claim limitation of, e.g., "0.98X."

The "CRISPR-Cas" system refers to a class of bacterial systems for defense against foreign nucleic acids. CRISPR-Cas systems are found in a wide range of eubacterial and archaeal organisms. CRISPR-Cas systems fall into two classes with six types, I, II, III, IV, V, and VI as well as many sub-types, with Class 1 including types I and III CRISPR systems, and Class 2 including types II, IV, V and VI; Class 1 subtypes include subtypes I-A to I-F, for example. See, e.g., Fonfara et al., *Nature* 532, 7600 (2016); Zetsche et al., *Cell* 163, 759-771 (2015); Adli et al. (2018). Endogenous CRISPR-Cas systems include a CRISPR locus containing repeat clusters separated by non-repeating spacer sequences that correspond to sequences from viruses and other mobile genetic elements, and Cas proteins that carry out multiple functions including spacer acquisition, RNA processing from the CRISPR locus, target identification, and cleavage. In class 1 systems these activities are effected by multiple Cas proteins, with Cas3 providing the endonuclease activity, whereas in class 2 systems they are all carried out by a single Cas, Cas9. Endogenous systems function with two RNAs transcribed from the CRISPR locus: crRNA, which includes the spacer sequences and which determines the target specificity of the system, and the transactivating tracrRNA. Exogenous systems, however, can function which a single chimeric guide RNA that incorporates both the crRNA and tracrRNA components. In addition, modified systems have been developed with entirely or partially catalytically inactive Cas proteins that are still capable of, e.g., specifically binding to nucleic acid targets as directed by the guide RNA, but which lack endonuclease activity entirely, or which only cleave a single strand, and which are thus useful for, e.g., nucleic acid labeling purposes or for enhanced targeting specificity. Any of these endogenous or exogenous CRISPR-Cas system, of any class, type, or subtype, or with any type of modification, can be utilized in the present methods. In particular, "Cas" proteins can be any member of the Cas protein family, including, inter alia, Cas3, Cas5, Cas6, Cas7, Cas8, Cas9, Cas10, Cas12 (including Cas12a, or Cpf1), Cas13, Cse1, Cse2, Csy1, Csy2, Csy3, GSU0054, Csm2, Cmr5, Csx11, Csx10, Csf1, Csn2, Cas4, C2c1, C2c3, C2c2, and others. In particular embodiments, Cas proteins with endonuclease activity are used, e.g., Cas3, Cas9, or Cas12a (Cpf1).

The term "nucleic acid sequence encoding a polypeptide" refers to a segment of DNA, which in some embodiments may be a gene or a portion thereof, that is involved in producing a polypeptide chain (e.g., an RNA-guided nuclease such as Cas9). A gene will generally include regions preceding and following the coding region (leader and trailer) involved in the transcription/translation of the gene product and the regulation of the transcription/translation. A gene can also include intervening sequences (introns) between individual coding segments (exons). Leaders, trailers, and introns can include regulatory elements that are necessary during the transcription and the translation of a gene (e.g., promoters, terminators, translational regulatory sequences such as ribosome binding sites and internal ribosome entry sites, enhancers, silencers, insulators, boundary elements, replication origins, matrix attachment sites and locus control regions, etc.). A "gene product" can refer to either mRNA or other RNA (e.g. sgRNA) or protein expressed from a particular gene.

The terms "expression" and "expressed" refer to the production of a transcriptional and/or translational product, e.g., of a nucleic acid sequence encoding a protein (e.g., a guide RNA or RNA-guided nuclease). In some embodiments, the term refers to the production of a transcriptional and/or translational product encoded by a gene (e.g., a gene encoding a protein) or a portion thereof. The level of expression of a DNA molecule in a cell may be assessed on the basis of either the amount of corresponding mRNA that is present within the cell or the amount of protein encoded by that DNA produced by the cell.

The term "recombinant" when used with reference, e.g., to a polynucleotide, protein, vector, or cell, indicates that the polynucleotide, protein, vector, or cell has been modified by the introduction of a heterologous nucleic acid or protein or the alteration of a native nucleic acid or protein, or that the cell is derived from a cell so modified. For example, recombinant polynucleotides contain nucleic acid sequences that are not found within the native (non-recombinant) form of the polynucleotide.

As used herein, the terms "polynucleotide," "nucleic acid," and "nucleotide," refer to deoxyribonucleic acids (DNA) or ribonucleic acids (RNA) and polymers thereof. The term includes, but is not limited to, single-, double-, or multi-stranded DNA or RNA, genomic DNA, cDNA, and DNA-RNA hybrids, as well as other polymers comprising purine and/or pyrimidine bases or other natural, chemically modified, biochemically modified, non-natural, synthetic, or derivatized nucleotide bases. Unless specifically limited, the term encompasses nucleic acids containing known analogs of natural nucleotides that have similar binding properties as the reference nucleic acid. Unless otherwise indicated, a particular nucleic acid sequence also implicitly encompasses conservatively modified variants thereof (e.g., degenerate codon substitutions), homologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "vector" and "expression vector" refer to a nucleic acid construct, e.g., plasmid or viral vector, generated recombinantly or synthetically, with a series of specified nucleic acid elements that permit transcription of a particular nucleic acid sequence (e.g., a guide RNA and/or RNA-guided nuclease) in a cell, e.g., a protoplast. In some embodiments, a vector includes a polynucleotide to be transcribed, operably linked to a promoter, e.g., a constitutive or inducible promoter. Other elements that may be present in a vector include those that enhance transcription (e.g., enhancers), those that terminate transcription (e.g., terminators), those that confer certain binding affinity or antigenicity to a protein (e.g., recombinant protein) produced from the vector, and those that enable replication of the vector and its packaging (e.g., into a viral particle). In some embodiments, the vector is a viral vector (i.e., a viral genome or a portion thereof).

The terms "polypeptide," "peptide," and "protein" are used interchangeably herein to refer to a polymer of amino acid residues. All three terms apply to amino acid polymers in which one or more amino acid residues are an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

3. Protoplast Isolation

The present methods involve the use of isolated protoplasts from grape plants for genomic modification and plant regeneration. Protoplasts can be isolated in a variety of ways. In particular embodiments, they are isolated from suspension cultures derived from, e.g., anther filaments. In some embodiments, the protoplasts are derived directly from a suspension culture. In some embodiments, they are derived from embryonic calli obtained by plating aliquots of suspension culture onto, e.g., an agar solidified medium.

Suspension cultures can be prepared using any suitable plant medium known in the art. In particular embodiments, liquid WPM medium (Woody Plant Medium, e.g., as described in Lloyd and McCown, 1981, the entire disclosure of which is herein incorporated by reference) is used. WPM can be supplemented with one or more additional reagents, such as sucrose, casein hydrolysate, Picloram, metatopolin, activated charcoal, ascorbic acid, reduced glutathione, or MES (2-(N-Morpholino) ethanesulfonic Acid). In one embodiment, a suspension culture is used that contains liquid WPM medium supplemented with, e.g., 20 g/liter sucrose, 1 g/liter casein hydrolysate, 10.0 mg/l Picloram, 2.0 mg/l metatopolin, 2 g/l activated charcoal, 100 mg/l ascorbic acid, and 120 mg/l reduced glutathione. In one embodiment, a suspension culture is used that contains WPM, 1 g/l casein, 1M MES, 1000 mg/l activated charcoal, 10 mg/l picloram, and 2 mg/l meta-topolin.

Suspension cultures can be grown in appropriate vessels and following standard methods, e.g., in 125 ml shake flasks on a gyratory shaker at 90 rpms in the dark.

In some embodiments, embryonic calli are generated from grape suspension cultures and subsequently used as a source of protoplasts. To generate calli from suspension cultures, an aliquot (e.g., 500 µl) of suspension culture can be plated onto agar-solidified medium, e.g., WPM medium supplemented with one or more additional components such as sucrose, casein hydrolysate, MES, Picloram, thidiazuron (TDZ), or activated charcoal. In one embodiment, agar-solidified medium is used that contains WPM medium supplemented with 20 g/liter sucrose, 1 g/liter casein hydrolysate, 10.0 mg/l Picloram, 2.0 mg/l TDZ, 2 g/l activated charcoal, 100 mg/l ascorbic acid and 120 mg/l reduced glutathione. In one embodiment, agar-solidified medium is used that contains WPM medium supplemented with 20 g/liter sucrose, 1 g/liter casein hydrolysate, 1 mM MES, 10.0 mg/l Picloram, 2.0 mg/l thidiazuron, and 2 g/l activated charcoal.

In some embodiments, embryonic calli generated following the plating of suspension culture onto agar-solidified medium are used for the isolation of protoplasts. In some embodiments, protoplasts are isolated from suspension cultures. For example, aliquots can be collected from rapidly dividing embryonic grape suspension cultures and centrifuged at 2000 rpm for about 8 minutes, to harvest about 3 ml of packed volume. The supernatant is then removed, replaced with about 5 ml of protoplast isolation solution, and the solution is transferred to, e.g., a petri dish.

Both sources of cells, i.e., from suspension cultures or from embryonic calli, can then be treated with an enzyme solution comprising, e.g., cellulose, pectinase, and macerozyme, to break down the cell wall and release the protoplasts. In one embodiment, a solution is used that comprises filter sterilized 0.5% Onozuka Cellulase R10 (or Onozuka Cellulase RS, 0.25%), 0.25% pectinase, 0.25% macerozyme R10, 0.4 M mannitol, 5 mM CaCl2, 10 g/l BSA, and 5 mM MES. In one embodiment, the cells are subjected to infiltration under vacuum, e.g., for 3×2-minute exposures, and incubated, e.g., at 25 degrees C. in the dark on a platform shaker at 50 rpms. After incubation, e.g., for about 16 hours, the solution containing the protoplasts is filtered, e.g., through a 40 µm screen, and protoplasts are collected by pelleting, e.g., at 2000 rpm for 10 minutes. The protoplasts can then be washed in an osmotically adjusted solution, e.g., washed twice in a solution containing mannitol, $CaCl_2$, BSA, and HEPES. In one embodiment, the solution contains 0.4-0.6 M mannitol, 2 mM CaCl2, 1 g/l BSA and 1,191 mg/l HEPES.

Following digestion of the cell wall, filtration, collection, and washing, the protoplasts are purified. In one embodiment, in particular for protoplasts isolated from calli, the purification is performed using a dextran gradient, e.g., a gradient consisting of 2 ml of a 13% dextran solution, overlaid with 1.5 ml of 0.4 M wash medium. The protoplast band can be harvested from the gradient, e.g., using a sterile Pasteur pipette and transferred to a petri dish. In another embodiment, in particular for protoplasts isolated from suspension culture, a gradient is used consisting of 4 ml of a 13% dextran solution, overlaid with a 3 ml of a 9.1% dextran solution, overlaid with 2 ml of a 4.05% dextran solution, overlaid with 1 ml of wash solution. When centrifuged at 2000 rpms for 8 minutes, the protoplasts layer at the interface of the 4.05% dextran layer and the wash solution, effectively separating the protoplasts with minimal contamination from the activated charcoal. In some embodiments, harvesting protoplasts from embryonic callus or suspension culture using the herein disclosed methods yields approximately 2.5-8×10⁶ cells/ml when starting with 500 mg fresh weight of embryonic callus or 3 ml packed suspension culture.

Protoplasts isolated from embryonic calli or suspension culture using the herein-disclosed methods, can then be genetically modified, encapsulated, and used to regenerate grape plants, as described in more detail elsewhere herein.

4. Genomic Modifications

Prior to encapsulation, protoplasts can be genetically modified using an RNA-guided nuclease, e.g. an endonuclease. In particular embodiments, a CRISPR-Cas system is used to modify one or more target genes in the genome of the protoplast. Other methods can also be used, e.g. transcription activator-like effector nucleases (TALENs), zinc-finger nucleases (ZFNs), and others. Any type of genetic modification can be performed, including insertions of one or more sequences into the protoplast genome, deletions of one or more sequences in the protoplast genome, replacement of one or more sequences in the protoplast genome, and alteration of one or more nucleotides in the protoplast genome.

In particular embodiments of the disclosure, a CRISPR-Cas system is used, e.g., Type II CRISPR-Cas system. The CRISPR-Cas system includes a guide RNA, e.g., sgRNA, that targets the genomic sequence to be altered, and a nuclease that interacts with the guide RNA and cleaves or binds to the targeted genomic sequence. The guide RNA can take any form, including as a single guide RNA, or sgRNA (e.g. a single RNA comprising both crRNA and tracrRNA elements) or as separate crRNA and tracrRNA elements. Standard methods can be used for the design of suitable guide RNAs, e.g., sgRNAs, e.g. as described in Cui et al. (2018) Interdisc. Sci.: Comp. Life Sci. 10(2):455-465; Bauer et al. (2018) Front. Pharmacol: 12 Jul. 2018, doi.org/10.3389/fphar.2018.00749; Mohr et al. (2016) FEBS J., doi.org/10.1111/febs.13777, the entire disclosures of which are herein incorporated by reference.

Any CRISPR nuclease can be used in the present methods, including, but not limited to, Cas9, Cas12a/Cpf1, or Cas3, and the nuclease can be from any source, e.g. *Streptococcus pyogenes* (e.g. SpCas9), *Staphylococcus aureus* (SaCas9), *Streptococcus* thermophiles (StCas9), *Neisseria meningitides* (NmCas9), *Francisella novicida* (FnCas9), and *Campylobacter jejuni* (CjCas9). The guide RNA and nuclease can be used in various ways to effect genomic modifications in the protoplast. For example, two guide RNAs can be used that flank an undesired gene or genomic sequence, and cleavage of the two target sites leads to the deletion of the gene or genomic sequence. In some embodiments, a guide RNA targeting a gene or genomic sequence of interest is used, and the cleavage of the gene or genomic sequence of interest and subsequent repair by the cell leads to the generation of an insertion, deletion, or mutation of nucleotides at the site of cleavage. In some such embodiments, one or more additional polynucleotides are introduced into the protoplast together with the guide RNA and nuclease, e.g., a polynucleotide comprising a sequence sharing homology to the targeted genomic sequence, and the one or more additional polynucleotides can effect a deletion, insertion, or alteration of the cleaved genomic sequence via homologous recombination (homology-directed repair).

In particular embodiments, one or more polynucleotides are introduced into the protoplasts encoding a guide RNA and encoding the RNA-guided nuclease, e.g., Cas9. For example, a vector, e.g. a viral vector, plasmid vector, or *Agrobacterium* vector, encoding one or more guide RNAs and an RNA-guided nuclease is introduced into the protoplasts, e.g., by transfection, wherein the one or more guide RNAs and the RNA-guided nuclease are expressed in the protoplasts. In some embodiments, one or more guide RNAs are preassembled with RNA-guided nucleases as ribonucleoproteins (RNPs), and the assembled ribonucleoproteins are introduced into the protoplasts.

The elements of the CRISPR-Cas system can be introduced in any of a number of ways. In some embodiments, the elements are introduced using polyethylene glycol (PEG), e.g., polyethylene glycol-calcium (PEG-Ca+). In some embodiments, the elements are introduced using electroporation. Other suitable methods include microinjection, DEAE-dextran treatment, lipofection, nanoparticle-mediated transfection, protein transduction domain-mediated transfection, and biolistic bombardment. Methods for introducing RNA-guided nucleases into protoplasts to effect genetic modifications that can be used include those disclosed in, e.g., Toda et al. (2019) Nature Plants 5(4):363-368; Osakabe et al. (2018) Nat Protoc 13(12):2844-2863; Soda et al. (2018) Plant Physiol Biochem 131:2-11; WO2017061806A1; the entire disclosures of which are herein incorporated by reference.

In particular embodiments, polynucleotides encoding the CRISPR-Cas system (e.g., guide RNA and a polynucleotide encoding a nuclease) are expressed in the protoplasts but are not integrated into the protoplast genome. As such, while the genomic modifications induced by the activity of the CRISPR-Cas system are maintained in the protoplast and in the cells of plants regenerated from the protoplast, the CRISPR-Cas system itself does not persist and does not induce further genomic modification.

5. Protoplast Culture

To generate plants from the isolated and genetically modified protoplasts, the protoplasts are encapsulated in a gel matrix and cultured. Encapsulation of the protoplasts provides numerous advantages. For example, it allows the isolation of each protoplast and thereby ensures that each protoplast-derived colony is of single-cell descent, which is particularly important in the context of gene editing. In the absence of encapsulation, protoplasts will clump together and thereby make the determination of single-cell descent impossible. In addition, encapsulation of protoplasts stimulates cell division in the cells, whereas normally non-encapsulated protoplasts cultured at low density fail to divide. The encapsulation is performed such that it allows passage of nutrients to the embedded protoplasts, meaning that the conditioned medium serves as a nurse culture for the protoplasts and that different media formulations can be tested.

Any of a number of materials can be used to encapsulate the protoplasts, so long that the material is stable under the culture conditions described herein, allows cell division in the protoplasts and generation of a callus, and allows passage of nutrients to encapsulated protoplasts. In particular embodiments, alginate is used. Other materials that can be used include, inter alia, agarose and other forms or derivatives of agar, carrageenan, chitosan, gellan gum, hyaluronic acid, collagen, gelatin, elastin, fibrin, silk fibroin, and others. See, e.g., Gasperini et al., (2014) J R Soc Interface 11(100): 20140817, the entire disclosure of which is herein incorporated in its entirety.

In some embodiments, to prepare beads from alginate or another material, the density of protoplasts is first adjusted to a desired level, e.g., approximately twice the desired final density in an appropriate buffer such as a 0.4 M mannitol buffer solution. For example, the density can be from $1\times10^6$ to $1\times10^8$ protoplasts/ml, or $5\times10^6$ to $5\times10^7$ protoplasts/ml. In one embodiment, the density is approximately $1\times10^7$ protoplasts/ml. The protoplast solution can then be mixed with, e.g., an equal volume of a solution containing the encapsulation material. In one embodiment, a protoplast solution containing approximately twice the desired final density of protoplasts is mixed with an equal volume of a sodium alginate solution, e.g., a 6.4% or 3.2% solution adjusted to, e.g., pH 5.7. Beads can be formed, e.g., by drawing the solution into a syringe and expelling the solution dropwise through a syringe needle into a solution containing $CaCl_2$), e.g., 50 mM $CaCl_2$). The size of the needle can be varied to adjust the size of the beads. For example, a 30.5 or 23 gauge needle can be used to make beads that are approximately 2 or 5 mm in diameter, respectively. Parameters such as the nature and concentration of the material used, the size of syringe needles, etc. can be varied to obtain beads with optimal nutrient diffusion and other desirable characteristics.

Protoplasts, e.g., encapsulated protoplasts, are then cultured in an osmotically conditioned medium or feeder suspension cultures in order to prevent them from implosion or explosion prior to the reformation of their cell walls. In particular embodiments, encapsulated protoplasts are cultured in an osmotically conditioned feeder suspension culture. Osmotically conditioned feeder suspensions can be generated, e.g., by gradually increasing the osmotic potential of the suspension medium over time. For example, half of the medium can be replaced bi-weekly with a grape suspension medium containing, e.g., 50-100 g/L or 72.87 g/L mannitol, 1000-1500 or 1191 mg/l HEPES, and BSA, e.g., 1 g/L, at an appropriate pH, e.g., 5.7. Repeating this process bi-weekly allows the protoplasts to gradually acclimate to the high osmotic medium over time.

In particular embodiments of the present methods, embedded protoplasts are cultured in feeder cell suspensions, wherein the encapsulated protoplasts undergo cell division and form callus colonies. In one embodiment, embedded protoplasts are resuspended in conditioned osmotically adjusted grape cell suspension cultures in an appropriate vessel, e.g., 125 mL shake flask, and incubated at, e.g., 100 rpm and 25 degrees C. Once protoplasts have begun dividing, e.g., after 14 days, the concentration of mannitol is gradually reduced. For example, following a starting concentration of 0.4 M mannitol, an equal volume of grape suspension culture medium can be added after 14 days to reduce the mannitol concentration to 0.2 M, and an equal volume can be added after an additional 14 days to reduce the concentration to 0.1 M. In some embodiments of the methods, encapsulated protoplasts initiate cell division within 7 days of being suspended in a feeder suspension culture. In some embodiments, small or mini callus colonies are formed within 21 days following encapsulation.

In some embodiments, protoplasts are cultured in plates such as 24-well plates, which allows the testing of multiple culture conditions, e.g., using different hormone or media formulations, for example to assess their ability to stimulate cell division.

In particular embodiments, one or more antioxidants are added to the culture medium or feeding suspension containing the encapsulated protoplasts. In one embodiment, the addition of one or more antioxidants to the culture medium or suspension leads to an increase in the number of calli generated per bead. Any of a number of antioxidants can be used, e.g., ascorbic acid, citric acid, reduced glutathione, L-cysteine, lipoic acid, uric acid, carotenes, α-tocopherol, ubiquinol, and others. In particular embodiments, the antioxidants include one or more of ascorbic acid, citric acid, reduced glutathione, and L-cysteine. In one embodiment, the antioxidants include 100 mg/l ascorbic acid, 150 mg/l citric acid, 30 mg/l reduced glutathione and 100 mg/l L-cysteine.

In particular embodiments, a polyamine is added to culture medium or feeding suspension containing the encapsulated protoplasts. In one embodiment, the addition of one or more polyamine to the culture medium or feeding suspension leads to an increase in the number and speed of callus formation from protoplasts. Any of a number of polyamines can be used, e.g., spermine, spermidine, tris(2-aminoethyl) amine, cyclen, 1,4,7-triazacyclononane, 1,1,1-tris(aminomethyl)ethane, and polyethylenimine. In a particular embodiment, the polyamine is spermine, e.g., 0.1-1 mM spermine, or 1 mM spermine.

In some embodiments, the culture medium or feeding suspension contains both one or more antioxidants and a polyamine. In a particular embodiment, the culture medium or feeding suspension contains ascorbic acid, citric acid, reduced glutathione, L-cysteine, and spermine.

Conditioned media suitable for the cultivation of protoplasts include, e.g., Nitsch and Nitsch minimal organics medium (1969) supplemented with 60 g/l sucrose, 1.0 mg/l 2,4-dichlorophenoxyacetic acid (2,4-D) and 2.0 mg/l benzylaminopurine (BAP) (PIV); MS minimal organics medium supplemented with 20 g/l sucrose 1.0 mg/l 2,4-D and 0.2 mg/l BAP (MSE); MS minimal organics medium supplemented with 30 g/l sucrose 1.0 mg/l 2,4-D and 1.0 mg/l BAP (MS1); and WPM medium supplemented with 20 g/l sucrose 10 mg/l Picloram and 2.0 mg/l TDZ (Pic/TDZ).

6. Plant Regeneration

Mini callus colonies generated from encapsulated protoplasts can then be transferred out of the culture medium or feeder suspension to allow further growth. In some embodiments, beads containing callus colonies of, e.g., 16-21 cells, are transferred to, e.g., a petri dish containing, e.g., minimal organics medium supplemented with one or more additional reagents such as sucrose, picloram, and TDZ. In one embodiment, the petri dish contains minimal organics medium supplemented with 30 g/l sucrose, 10 mg/l Picloram and 2.0 mg/l TDZ. In some embodiments, the beads are transferred one or more additional times, to eliminate any feeder suspension cells.

After washing, the beads can be transferred to a solid medium, e.g., transferred to a feeder agar-solidified petri dish containing minimal organics medium supplemented with, e.g., sucrose, picloram, and TDZ. In one embodiment, the dish contains Lloyd and McCown minimal organics medium supplemented with 30 g/l sucrose, 10 mg/l Picloram and 2.0 mg/l TDZ, onto which a 1103P grape cell suspension, e.g., 1.0 ml, is plated. In one embodiment, a first filter, e.g., 85 mm Whatman filter paper, is placed over the plated suspension, and a second filter, e.g., 70 mm Whatman filter paper, is placed on top of the first filter, and the beads are placed on top of the second filter. The plates can be supplemented with additional medium, e.g., Lloyd and McCown minimal organics medium supplemented with 30 g/l sucrose, 10 mg/l Picloram and 2.0 mg/l TDZ, to prevent desiccation.

In some embodiments, the alginate bead or other gel matrix is dissolved prior to plant regeneration. To dissolve alginate beads, for example, the washed beads can be transferred to a flask, e.g., a 125 ml shake flask, containing $KH_2PO_4$, e.g. 20 ml of a 300 mM $KH_2PO_4$ solution. Beads and solution can be pipetted up and down repeatedly (e.g., up to 10 times) through, e.g., a 10 ml pipet, to break up the alginate matrix. The flask can then be placed on a gyratory shaker at, e.g., 100 rpm overnight. After 16 to 24 hours, the suspension is again pipetted up and down through a pipet (e.g., 10 ml pipet), to compete the dissolution of the matrix and release the protoplast-derived callus colonies. Suspensions containing the dissolved protoplast-derived calli can then be centrifuged at, e.g., 2000 rpms for 8 minutes, and the potassium phosphate solution removed. The calli can then be resuspended, e.g., in Lloyd and McCown minimal organics medium supplemented with 30 g/l sucrose, 10 mg/l Picloram and 2.0 mg/l TDZ.

In some embodiments, the calli are transferred without dissolving the alginate matrix. For example, once protoplasts have developed into callus colonies of approximately 16 to 32 cells within the alginate beads (approximately day 40 to 50), the beads can be transferred with the conditioned feeder suspension into a 100×20 mm petri dish, e.g., using forceps and transferring individual beads to a 100×20 mm petri dish containing 40 ml of Lloyd and McCown minimal organics medium supplemented with 20 g/l sucrose, 1 g/l casein, 222 mg/l $CaCl_2$, without hormones or activated charcoal. The transfer/washing process can be repeated, e.g., two more times to eliminate any of the feeder suspension cells, and the beads then transferred onto agar-solidified 100×20 mm feeder plates containing 40 ml of Lloyd and McCown minimal organics medium supplemented with 20 g/l sucrose, 50 g/l sorbitol, 1 g/l casein, 1 mM MES, 0.5 mg/l BAP and 0.1 mg/l NAA onto which 1.0 ml of a 1103P grape suspension culture is plated. The grape suspension culture medium can consist, e.g., of WPM medium supplemented with 20 g/l sucrose 10 mg/l picloram and 2.0 mg/l TDZ, 72.87 g/L mannitol, 222 mg/l $CaCl_2$, 1 g/l casein, 1,191 mg/l HEPES and 2 g/l activated charcoal, pH 5.7. An 85 mm Whatman filter paper can be placed over the plated suspension and a 70 mm Whatman filter paper on top of the 85 mm filter, and then beads placed on top of the 70 mm filter paper. In some embodiments, 1 ml Lloyd and McCown minimal organics medium supplemented with 30 g/l sucrose, 1 g/l casein, 1 mM MES, 10 mg/l picloram and 2.0 mg/l TDZ is added to each plate to prevent desiccation. The cultures can then be incubated, e.g., at 26 degrees centigrade in the dark. Using such methods, mini-calli can develop into somatic embryos within the beads after approximately 3-4 weeks.

After a suitable period of time, e.g., about 4 weeks, the beads containing the mini calli are transferred to a solid medium, e.g., agar-solidified plant medium supplemented with one or more components such as sucrose, casein, MES, activated charcoal, BAP, NAA, and sorbitol, and allowed to develop somatic embryos. In one embodiment, the solid medium contains agar solidified WPM (woody plant medium) supplemented with 20 g/l sucrose, 1 g/l casein, 1 mM MES, 500 mg/l activated charcoal, 0.5 mg/l BAP, 0.1 mg/l NAA 50 g/l sorbitol and 14 g/l agar.

Once the embryos have formed, the beads can be transferred to another solid plant medium, e.g., agar-solidified plant medium supplemented with one or more components such as sucrose, casein, MES, charcoal, BAP, sorbitol, and agar, and allowed to germinate and develop into plants. In one embodiment, the solid plant medium contains agar solidified WPM supplemented with 20 g/l sucrose, 1 g/l casein, 1 mM MES, 500 mg/l activated charcoal, 0.5 mg/l BAP, 0.1 mg/l NAA 0.0 g/l sorbitol and 7 g/l agar. In particular embodiments, the plant medium does not comprise sorbitol.

In some embodiments, protoplast-derived grape embryos are maintained or stored in a dormant state for an indefinite period of time. For example, if the beads are maintained on agar-solidified medium containing sorbitol, the embryos do not germinate further and become dormant. This property allows embryos to be stored, e.g., embryos from gene editing studies, which can be germinated as needed, e.g., for genetic analysis. Subsequently, germination and plant production can be stimulated from the protoplast-derived dormant somatic embryos by transferring the embryo-containing alginate beads to medium lacking sorbitol (e.g., plant medium without sorbitol), on which they germinate and develop into whole plants.

7. Kits

In another aspect, kits are provided herein. In some embodiments, the kit comprises one or more element for producing genetically modified grape plants according to the present invention. The kit can comprise, e.g., one or more elements described herein for practicing the present methods, including an isolated protoplast, an anther filament, a guide RNA, an RNA-guided nuclease, a CRISPR-Cas RNP, culture medium, transfection reagents, etc.

Kits of the present invention can be packaged in a way that allows for safe or convenient storage or use (e.g., in a box or other container having a lid). Typically, kits of the present invention include one or more containers, each container storing a particular kit component such as a reagent, an isolated protoplast, and so on. The choice of container will depend on the particular form of its contents, e.g., a kit component that is in liquid form, powder form, etc. Furthermore, containers can be made of materials that are designed to maximize the shelf-life of the kit components. As a non-limiting example, kit components that are light-sensitive can be stored in containers that are opaque.

In some embodiments, the kit contains one or more containers or devices, e.g. petri dish, Nalgene jars (e.g., 60 ml Nalgene jars), flask, syringe, for practicing the present methods. In yet other embodiments, the kit further comprises instructions for use, e.g., containing directions (i.e., protocols) for the practice of the methods of this invention (e.g., instructions for using the kit for isolating protoplasts, regenerating plants, effecting genomic modifications on an isolated protoplast). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

8. EXAMPLES

The following examples are offered to illustrate, but not to limit, the claimed invention.

Example 1. Grape Protoplast Isolation and Regeneration of Plants for Use in Gene Editing Technology Introduction The development of a system that achieves the successful isolation of grape protoplasts, the formation of callus from those protoplasts, and ultimately the regeneration of protoplast-derived plants has significant relevance to the PD/GWSS Research Community and the wine-grape industry. It provides an excellent vehicle for deploying non-*Agrobacterium*-mediated non-integrating gene editing technology for fundamental research and product development. Even if the goal of regeneration of plants from protoplasts is not achieved, efficient formation of protoplast-derived callus can be used for high throughput testing of potential gene editing guide RNAs. If regeneration of whole plants can be achieved, it will allow for the production of non-chimeric gene edited plants, which is critical for clonally propagated crops such as grape.

Protoplast technology was actively researched in the 1980s and early 1990s, but the advent of transgenic technology resulted in this cell culture technique falling out of favor. Although there are published reports in the literature demonstrating successful isolation of protoplasts from grapes, production of callus from grape protoplasts has historically proven to be inefficient (Xu et al., 2007). In addition, to our knowledge, regeneration of grape plants from protoplasts has not yet been achieved. We believe that utilizing embryogenic callus and rapidly dividing grape suspension cultures may provide advantages over other tissue sources. Given that embryogenic callus and suspension cultures are highly efficient at regenerating embryos and plants, and given that the protoplasts will be produced directly from these tissues, we believe this material gives us the best possibility of regenerating embryos and plants from protoplast-derived callus. Encapsulating protoplasts in alginate beads and culturing them in conditioned medium or nurse cultures has enhanced the frequency of protoplast division in other crops. We have demonstrated that this technique is applicable for culturing grape protoplasts. Encapsulation of protoplasts in alginate beads allows us to test many different media components by culturing beads in a 24-well plate format, which allows us to test media addendums using a factorial design. We have develop a robust grape protoplast isolation and purification system which routinely produced high yields of protoplasts from embryogenic callus of the three grape genotypes we tested; Merlot, Thompson Seedless and 1103P. By encapsulating protoplasts in a calcium alginate matrix and culturing them in osmotically adjusted grape feeder cell suspensions, we can routinely stimulate callus development from isolated protoplast. We have discovered that the addition of antioxidants and polyamines to the culture medium significantly improves callus formation from protoplasts. We are now in the process of testing various media formulations in an effort to regenerate plants from protoplast-derived callus.

Figure 2:
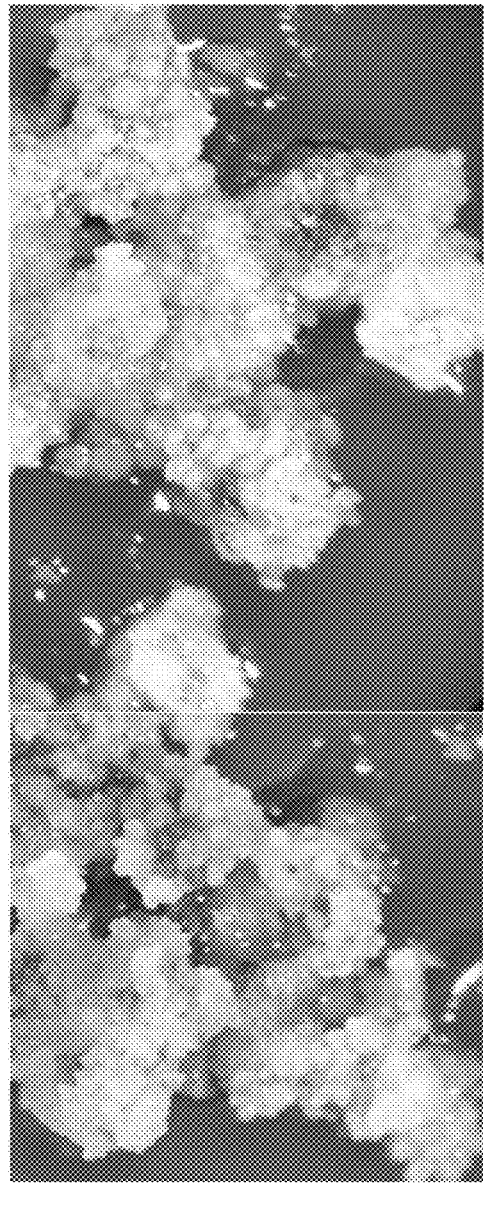
FIG. 2. Embryogenic callus generated by plating a 200 µl aliquot of grape suspension culture onto agar solidified WPM medium (Lloyd and McCown, 1981) supplemented with 20 g/liter sucrose, 1 g/liter casein hydrolysate, 1 mM MES, 10.0 mg/l Picloram, 2.0 mg/l thidiazuron, and 2 g/l activated charcoal (PIC/TDZ).

Part 1: Protoplast Isolation Techniques for Grape Using Actively Dividing Grape Cultures In 2019, we collected immature flowers from the Foundation Plant Service's vineyards for Chardonnay, 1103P, and Thompson Seedless, and plated anther filaments to generate new embryogenic cultures to serve as a new source material from which to isolate protoplasts and to establish new conditioned feeder suspensions. We are particularly interested in generating callus from Chardonnay. Chardonnay has proven difficult to modify using *Agrobacterium*-mediated transformation and would therefore benefit from protoplast-mediated gene editing. Furthermore, Chardonnay produces fewer phenolic compounds in culture than other grape varietals, which makes it a particularly good candidate for protoplast culture. We harvest callus for Chardonnay anther filaments and bulk it up for use in protoplast culture. New cultures of 1103 are used to establish new embryogenic conditioned nurse suspension cultures (FIGS. 1, 2). We use the new Thompson seedless callus to generate somatic embryos cultures for use in studies on the development of protoplast isolation, culture and plant regeneration.

We collected aliquots of 1103, merlot and Thompson seedless suspensions and plated them on agar-solidified WPM medium (Lloyd and McCown, 1981) supplemented with 20 g/liter sucrose, 1 g/liter casein hydrolysate, 1 mM MES, 10.0 mg/l Picloram, 2.0 mg/l thidiazuron, 2 g/l activated charcoal (PIC/TDZ), in order to generate embryogenic callus cultures which are used for the isolation of grape protoplasts (FIG. 2).

Figure 3:
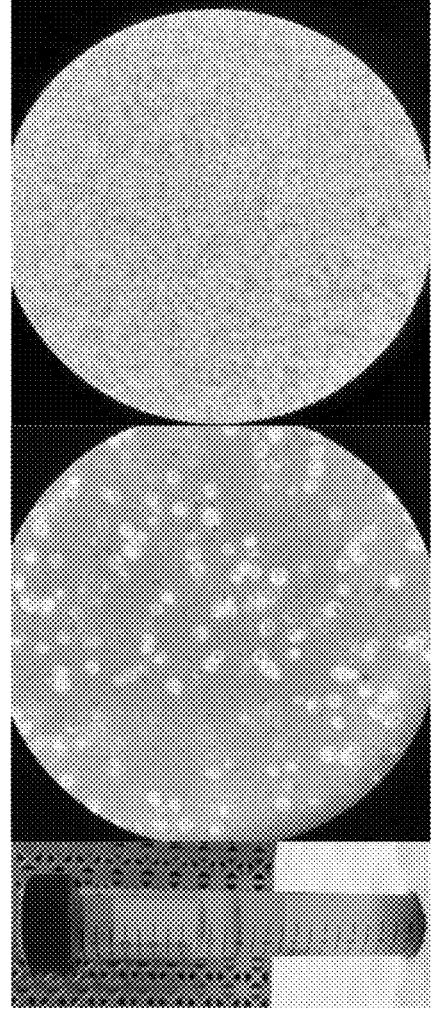
FIG. 3. Dextran gradient separates grape protoplasts from debris (left). Harvested Merlot (middle) and Thompson Seedless (right) grape protoplast prior to encapsulation in calcium alginate beads.

We harvest embryogenic callus of Merlot or Thompson Seedless from agar-solidified plates containing Pic/TDZ medium. We treated cells in an enzyme solution consisting of filter-sterilized 0.5% Onozuka Cellulase R10, 0.25% pectinase, 0.25% macerozyme R10, 0.4 M mannitol, 5 mM CaCl$_2$, 10 g/l BSA, and 5 mM MES. We subjected the cells to infiltration under house vacuum for three, 2-minute exposures and incubated the solution in the dark at 25 degrees centigrade on a platform shaker at 50 rpms. After approximately 16 hours incubation, we filtered the protoplast solution through a 40 μm screen and collected the protoplasts by pelleting via centrifugation at 700×g for 10 minutes. We washed the protoplasts twice in an osmotically adjusted wash solution containing 0.4 M mannitol, 2 mM CaCl$_2$, 1 g/l BSA and 1,191 mg/l HEPES. We purify protoplasts derived from embryogenic callus harvested from agar-solidified Pic/TDZ medium using a dextran gradient consisting of 2 ml of a 13% dextran solution, overlaid with 1.5 ml of 0.4 M wash solution. We can readily harvest the protoplast band, and we transferred them to a 60×15 mm petri dish using a Pasteur pipette. Yields of protoplasts from 500 mg fresh weight of embryogenic callus ranged from 2.5 to 8×10$^6$ cells per ml (FIG. 3).

Part 2: Culturing Grape Suspension Protoplasts in Calcium Alginate Beads and Stimulating the Formation of Callus Colonies.

Generating Osmotically Adjusted Conditioned Medium

The Plant Transformation Facility at UC Davis has developed a method for encapsulating protoplasts in calcium alginate beads and culturing them in an osmotically conditioned feeder suspension culture. The feeder suspension is used to stimulate the protoplasts to divide to form calli even at low protoplast culture density. We have demonstrated this to be efficacious in soybean (Tricoli et al., 1986) and lettuce protoplasts. Protoplasts need to be cultured in high osmotic medium to avoid implosion or explosion prior to the reformation of their cell walls. The conditioned media we are testing are based on formulations used to stimulate somatic embryo development from isolated grape anther filaments. These include:

Nitsch and Nitsch minimal organics medium (1969) supplemented with 60 g/l sucrose, 1.0 mg/l 2,4-dichlorophenoxyacetic acid (2,4-D) and 2.0 mg/l benzylaminopurine (BAP) (PIV)

MS minimal organics medium supplemented with 20 g/l sucrose 1.0 mg/l 2,4-D and 0.2 mg/l BAP (MSE)

MS minimal organics medium supplemented with 30 g/l sucrose 1.0 mg/l 2,4-D and 1.0 mg/l BAP (MS1)

WPM medium supplemented with 20 g/l sucrose 10 mg/l Picloram and 2.0 mg/l TDZ (Pic/TDZ)

We generated osmotically conditioned grape feeder suspensions of Thompson Seedless and 1103P by gradually increasing the osmotic potential of the suspension medium over time. During the bi-weekly subcultures of the suspension cultures, we removed one-half of the suspension and replaced it with grape suspension medium containing 72.87 g/L mannitol, 1191 mg/l HEPES and 1 g/L BSA, pH 5.7 along with the appropriate plant growth regulators. During the subsequent bi-weekly subculture, we again removed one-half of the old suspension and replaced it with an equal volume of medium containing 72.87 g/L mannitol, 1191 mg/l HEPES and 1 g/L BSA, pH 5.7. We repeated this process bi-weekly so the cells could gradually acclimate to the high osmotic medium over time.

Encapsulating the Protoplasts

Figure 4:
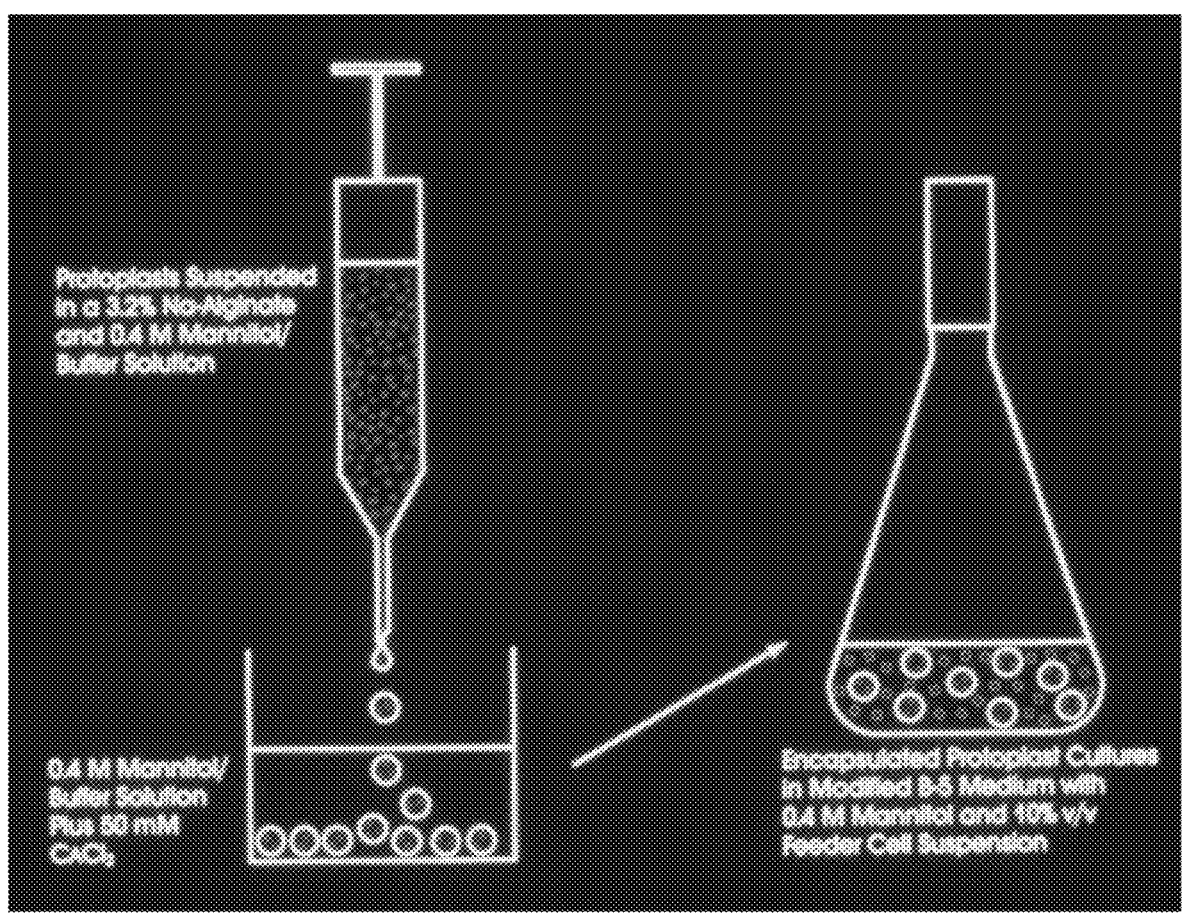
FIG. 4. Diagram of the production of protoplasts encapsulated in alginate beads and cultured in conditioned medium.

In order to generate the protoplast containing alginate beads, we adjusted the protoplast density to two times the desired final density with 0.4 M mannitol/buffer solution. We mixed the protoplast solution with an equal volume of a 6.4% or 3.2% sodium alginate solution (adjusted to pH 5.7). We formed beads by drawing up the solution into a 12 ml sterile syringe and expelling the solution dropwise through a syringe needle into an osmotically adjusted 50 mM $CaCl_2$) solution. After 30 minutes in the $CaCl_2$) solution, we rinsed the beads one time in 0.4 M mannitol/buffer wash solution (FIG. 4). The size of the beads can be increased or decreased depending on the gauge of the needle. We used either a 30.5 or 23-gauge needle to make beads that were approximately 2 mm or 5 mm in diameter respectively. We have also modified the gel strength of the beads by using either 6.4% or 3.2% sodium alginate. Varying both bead size and alginate concentration can affect the diffusion of nutrients into the beads.

In addition to allowing one to test various media formulations, embedding protoplasts in calcium alginate beads also ensures that each protoplast-derived callus colony is from single cell descent. This is important for gene editing experiments since if protoplasts are not fixed in a matrix, they will rapidly clump together, making determining single cell descent impossible.

Normally when cultured at low density, protoplasts fail to divide. However, culturing embedded protoplasts in conditioned medium or with feeder suspensions has been shown to stimulate protoplasts division in other species even at very low cell densities. Since the alginate matrix is permeable to nutrients, the conditioned medium serves as a nurse culture for the low-density cultured protoplasts. Previously, we have demonstrated that a single protoplast encapsulated in a 2-5 mm alginate bead could be stimulated to divide using this nurse culture system for both soybean and lettuce.

We have successfully embedded grape protoplasts of 1103P, Thompson Seedless and Merlot in calcium alginate beads and they have survived the embedding process. We initially cultured the embedded protoplasts in 24-well plates, which allowed us to test multiple hormone and media formulations for their ability to stimulate cell division using a factorial design. We placed one ml of medium osmotically adjusted with 0.4 M mannitol into each well along with 10-20 beads and incubated the plate in the dark on a platform shaker at 50 rpms. After 14 days, we added 1 ml of medium of the same formulation but lacking mannitol to each well, thereby reducing the osmotic of the medium in half. We monitored protoplasts for cell wall formation and division over a 4-6 week period. Using this system, we tested the osmotically adjusted media formulations of Gamborg et al., 1968, Chee, and Pool, 1987, Driver and. Kuniyuki, 1984, Lloyd and McCown, 1981, Murashige and Skoog, F., 1962, Quoirin, Lepoivre 1977, Rugini, 1984, and Schenk, and Hildebrandt, 1972. We also tested a wide array of hormone combination using the 24-well format, which allows for a two- or three-dimensional factorial design. Using this design, we were able to quickly test over 150 different combinations of hormones and 8 different salt formulations. To date, we observed the highest amount of cell wall formation and first cell divisions on Murashige and Skoog and Lloyd and McCown medium. We also tested media known to stimulate embryogenic callus formation from anther filament tissue. We collected conditioned PIV, MES, MS1, and Pic TDZ cell suspension cultures that had been acclimated to growing under high osmotic as described above, pelleted the cells by centrifugation, transferred 1 ml of this medium to 24 well plates and cultured encapsulated protoplasts in the wells. We found that the best-conditioned medium for stimulating protoplast cell division was Pic/TDZ, and this formulation was advanced to studies involving cell suspension feeder cultures in 125 ml shake flasks.

The system has also allowed us to rapidly test non-hormonal medium addendums including putrescene, spermidine, pluronic F68, resveratrol, citric acid, ascorbic acid, L-cysteine and reduced glutathione, either alone or in various combinations. Although this 24-well format allows us to observe protoplast viability, cell wall formation, and the first few cell divisions, the number of protoplasts that divide is low. In addition, although cells underwent a few divisions in 24-well plates, they failed to advance beyond the four to eight cell stage. Still, this 24-well format allowed us to determine which salt formulations, hormone combinations, and non-hormone addendum to advance to feeder suspension studies.

Figure 5:
FIG. 5. First cell division of a Thompson Seedless protoplast embedded within a calcium alginate bead (left) multi-cell stage (middle-left), Thompson seedless (middle-right) and Merlot (right) protoplasts forming mini callus colonies.

Development of Mini-Calli from Encapsulated Protoplasts Using Nurse Feeder Suspensions Using feeder cell suspension, we have made significant advances in stimulating isolated protoplasts to divide and form callus. The use of a feeder suspension greatly improved cell division and callus colony formation from protoplasts when compared to conditioned medium alone. We re-suspended embedded protoplasts in conditioned osmotically adjusted grape cell suspension cultures in 125 ml shake flasks and incubated them at 100 rpm and 25 degrees centigrade. In this system, we utilize a grape nurse suspension culture that is of a different genotype than the genotype used to generate the protoplasts. For example, we used 1103P conditioned cell suspension cultures for embedded Thompson Seedless protoplasts. Viable protoplasts began dividing in 4-7 days. We added equal volume of grape suspension culture medium without mannitol to the flasks at day 14, thereby reducing the starting mannitol concentration to 0.2 M. After 14 additional days, we again added equal volume of grape suspension culture medium without mannitol to the flasks, thereby reducing the starting mannitol concentration to 0.1 M. By day 21 post encapsulation, small callus colonies were visible (FIG. 5).

Recently, we have replaced the use of the shake flasks with 60×15 mm petri plates. This format allows for easy observation of the protoplasts using an inverted microscope and aids sampling of beads to evaluate the fate of the grown in feeder cultures with the antioxidant addendum (Table 1). We also observed increased Thompson seedless protoplast viability and increased callus development with increasing antioxidant concentrations (Table 2).

TABLE 1

Addition of antioxidant solution consisting of 100 mg/l ascorbic acid, 150 mg/l citric acid, 30 mg/l reduced glutathione and 100 mg/l L-cysteine enhances protoplast-derived callus formation.
Number of callus colonies per bead

| Bead | TS wo/anti-oxidants | TS w/1x anti-oxidants | Merlot w/o anti-oxidants | Merlot w/1x anti-oxidants |
|---|---|---|---|---|
| 1 | 13 | 45 | 0 | 199 |
| 2 | 42 | 52 | 0 | 182 |
| 3 | 27 | 37 | 0 | 159 |
| 4 | 30 | 36 | 0 | 160 |
| 5 | 30 | 69 | 0 | 139 |
| Ave | 28.4 | 47.8 | 0 | 167.8 | embedded protoplasts. Beads are cultured in 3.5 ml of Lloyd and McCown minimal organics medium supplemented with 30 g/l sucrose, 10 mg/l Picloram and 2.0 mg/l TDZ, 0.4 M mannitol, 1,191 mg/l HEPES, 50 mM CaCl2, 5× antioxidant solution with 1.5 ml of conditioned 1103P cell suspension culture.

Antioxidants

Callus colonies that develop in alginate beads often became discolored due to phenolic production. We were concerned that these compounds might be toxic to the growth and development of the protoplast-derived callus. We have developed and tested an antioxidant solution consisting of 100 mg/l ascorbic acid, 150 mg/l citric acid, 30 mg/l reduced glutathione and 100 mg/l L-cysteine (PTF AO). We tested the effect of this antioxidant addendum on protoplast viability and division on Thompson seedless and merlot protoplast cultures. Protoplasts were isolated and encapsulated in 1.6% calcium alginate beads. Calcium alginate beads from the same protoplast preparation were randomly transferred to shake flasks containing conditioned 1103P feeder cell suspensions with or without the addition of 1× or 5× of the antioxidant solutions. After 14 days, the osmotic strength of the feeder suspension was reduced from 0.4 M to 0.2 M mannitol. At day 35, we randomly harvested five beads per treatment and counted the number of mini calli per bead. For both merlot and Thompson seedless protoplasts, a significantly higher percentage of callus colonies were observed developing in beads grown in the suspensions containing the antioxidant solution (Table 1). Merlot protoplasts tend to produce more phenolic than Thompson seedless protoplasts and the antioxidant addendum had a much more profound effect on the division of the merlot protoplasts than the Thompson seedless protoplasts. Without the addition of the antioxidant mixture, no mini calli were observed after 35 days in culture, whereas an average of 168 mini calli were produced per bead from protoplasts

TABLE 2

Increasing the concentration of the antioxidant formulation consisting of 100 mg/l ascorbic acid, 150 mg/l citric acid, 30 mg/l reduced glutathione and 100 mg/l L-cysteine from 1x to 5x enhances protoplast-derived callus formation in Thompson seedless protoplasts.

| Bead | TS w/1x anti-oxidants | TS w/5x anti-oxidants |
|---|---|---|
| 1 | 2 | 112 |
| 2 | 6 | 114 |
| 3 | 10 | 130 |
| 4 | 10 | 118 |
| 5 | 13 | 125 |
| Ave | 8.2 | 119.8 |

Figure 6:
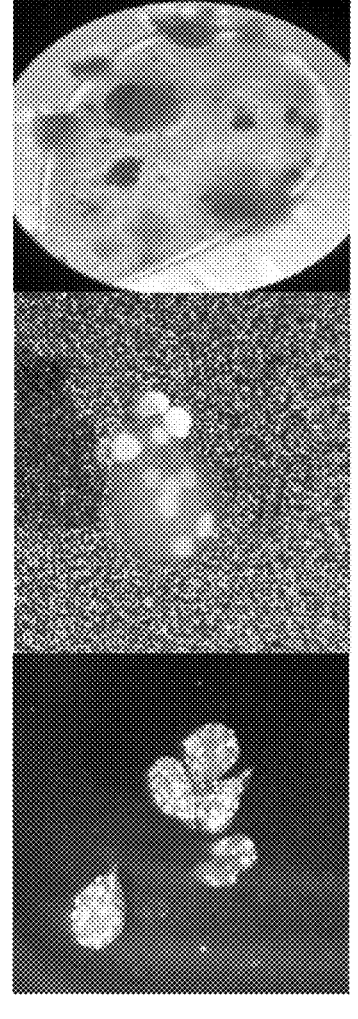
FIG. 6. Mini colonies from Thompson seedless protoplasts encapsulated in calcium alginate beads and grown in conditioned cell suspension of 1103P (left). Callus colonies growing out of the alginate matrix (middle). Close up of an individual bead from experiment 18340 with developing callus colonies 6 weeks after encapsulation (right).

Callus colonies continued to develop within the calcium alginate beads and often grew large enough that they could be seen rupturing through the surface of the beads (FIG. 6). Once protoplasts reached this stage, we dissolve the calcium alginate matrix to release the callus colonies.

Polyamines

Polyamines are polycationic compounds, which effect many aspects of growth and stress response in plants including cell division, embryogenesis, organogenesis, floral, fruit and pollen development and senescence. The major polyamines in plants include Putrescine (PUT) spermidine (SPD), spermine (SPM), and cadaverine (CAD).

Figure 7:
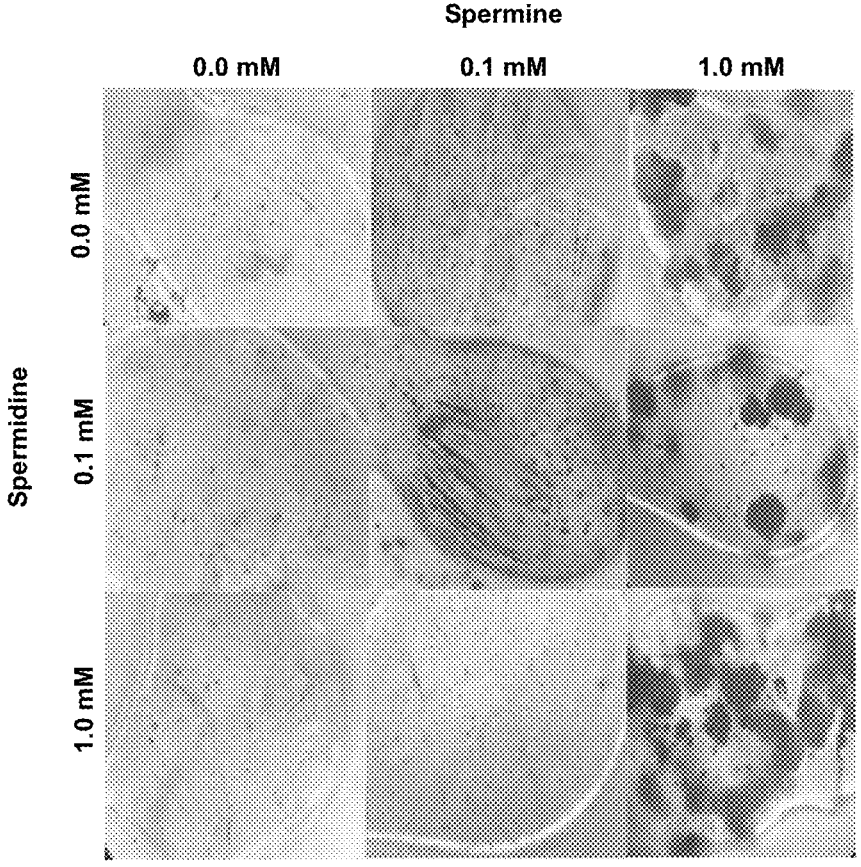
FIG. 7. Enhanced growth of TS mini calli when grown in the presence of 0.0, 0.1 or 1.0 mM spermidine in combination with 0.0. 0.1 or 1.0 mM spermine 21 days post encapsulation. All treatments also contained 1.0 mM putrescine and 5× antioxidant solution.

We are testing the ability of these polyamines to increase the plating efficiency of encapsulated protoplast as well as increase the rate of cell division. Initially we tested 1.0 mM putrescine in combination with 0.0 or 0.1 mM spermidine since we have previously found these levels to be beneficial in other plant species. We found the inclusion of 1.0 mM putrescine stimulated callus colony formation but the addition of 0.1 mM spermidine did not enhance the response. We also tested 1.0 mM putrescine in combination with 0.0, 0.1 and 1.0 mM spermine and 0.0 0.01 or 1.0 mM spermidine. Interestingly, we have found that the addition of 1.0 mM spermine to the medium enhanced the number of protoplasts that divided and the speed of protoplast derived callus formation irrespective of the spermidine concentration. Very large multicellular colonies developed within 21 days of protoplast isolation. We did not see any enhancement in growth with the addition of 0.1 mM spermine (Table 3, FIG. 7).

TABLE 3

Callus colony formation 14 days after encapsulation of TS protoplast in calcium alginate beads
and grown in conditioned 0.4M Pic/TDZ 1103P feeder cell suspensions containing 1 mM putrescine, and
varying levels of spermidine (SPD) and spermine (SPM).
colonies/alginate bead Experiment 19129

| | | Bead | | | | | | |
| | 1 | 1 | 2 | 3 | 4 | 5 | Total | Average |
| --- | --- | --- | --- | --- | --- | --- | --- | --- |
| mM Polyamine | | | | | | | | |
| SPD | SPM | | | | | | | |
| 0.0 | 0.0 | 28 | 49 | 48 | 39 | 25 | 164 | 32.9 |
| 0.1 | 0.0 | 91 | 93 | 120 | 110 | 93 | 507 | 101.4 |
| 1.0 | 0.0 | 81 | 97 | 79 | 125 | 89 | 471 | 94.2 |
| 0.0 | 0.1 | 96 | 81 | 79 | 59 | 84 | 399 | 79.8 |
| 0.1 | 0.1 | 135 | 119 | 79 | 130 | 85 | 548 | 109.6 |
| 1.0 | 0.1 | 147 | 107 | 103 | 137 | 90 | 584 | 116.8 |
| 0.0 | 1.0 | 275 | 126 | 238 | 169 | 221 | 1029 | 205.8 |
| 0.1 | 1.0 | 219 | 168 | 154 | 84 | 188 | 813 | 162.6 |
| 1.0 | 1.0 | 212 | 262 | 196 | 220 | 162 | 1052 | 210.4 |

Figure 8:
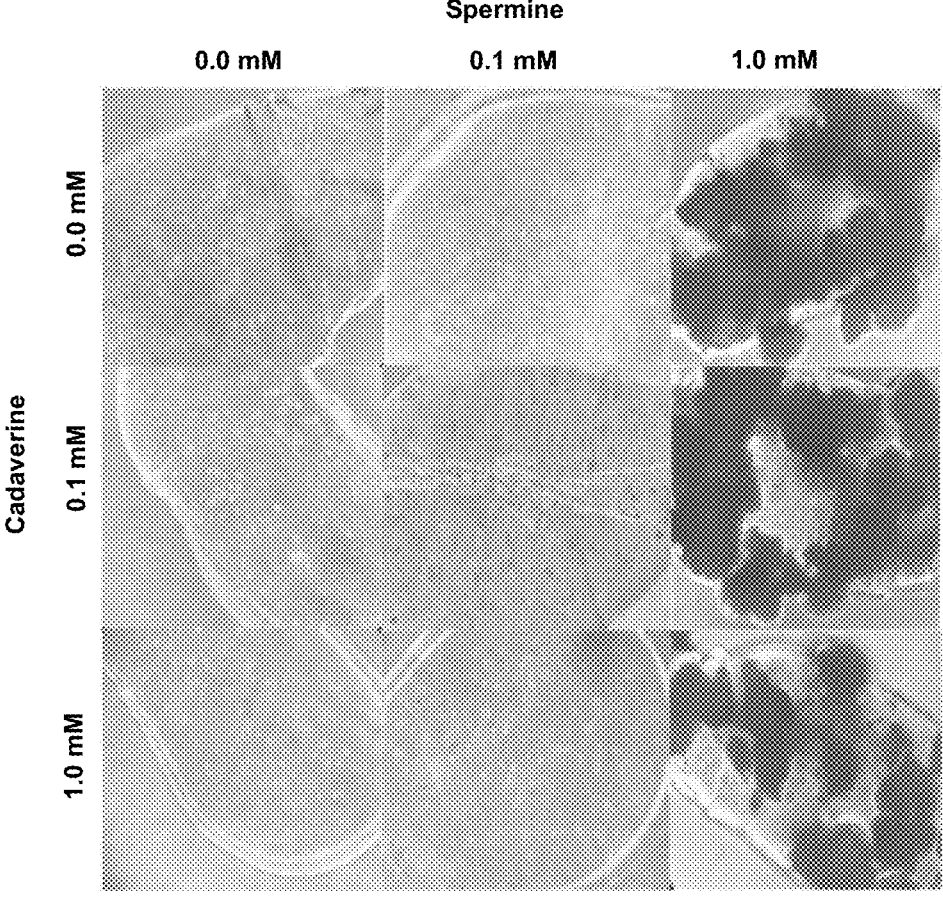
FIG. 8. Enhanced growth of TS mini calli when grown in the presence of 0.0, 0.1 or 1.0 mM Cadaverine in combination with 0.0. 0.1 or 1.0 mM spermine 14 days post encapsulation. All treatments also contained 1.0 mM putrescine, 0.1 mM spermidine, and 5× antioxidant solution.

We also tested cadaverine at 0.0, 0.1 or 1.0 mM in combination with 1.0 mM putrescine, 0.1 mM spermidine, and 0.0, 0.1 or 1.0 mM spermine. Cadaverine does not seem to enhance cell division or cells growth from grape protoplasts. However, we again saw a significant enhancement in callus colony growth with treatments that contained 1.0 mM spermine after only 21 days of culture regardless of the level of CAD tested (Table 4, FIG. 8).

overnight. After 16 to 24 hours, we again pipetted the suspension up and down through a 10 ml pipet, which competed the dissolution of the matrix, releasing the protoplast-derived callus colonies. We centrifuged suspensions containing the dissolved protoplast-derived calli at 2000 rpms for 8 minutes and removed the potassium phosphate solution. We re-suspended the calli in Lloyd and McCown minimal organics medium supplemented with 30 g/l

TABLE 4

Callus colony formation 14 days after encapsulation of TS protoplast in calcium alginate beads
and grown in conditioned 0.4M Pic/TDZ 1103P feeder cell suspensions containing 1.0 mM putrescine, 0.1
mM spermidine (SPD) and varying levels of spermine (SPM) and Cadaverine (CAD).
colonies/alginate bead Experiment 19136

| | | Bead | | | | | | |
| | 1 | 1 | 2 | 3 | 4 | 5 | Total | Average |
| --- | --- | --- | --- | --- | --- | --- | --- | --- |
| mM Polyamine | | | | | | | | |
| SPD | CAD | | | | | | | |
| 0.0 | 0.0 | 99 | 103 | 116 | 67 | 73 | 458 | 91.6 |
| 0.1 | 0.0 | 68 | 79 | 64 | 65 | 86 | 362 | 72.4 |
| 1.0 | 0.0 | 133 | 121 | 115 | 133 | 98 | 600 | 120 |
| 0.0 | 0.1 | 100 | 115 | 92 | 104 | 95 | 506 | 101.2 |
| 0.1 | 0.1 | 90 | 85 | 71 | 66 | 79 | 391 | 78.2 |
| 1.0 | 0.1 | 154 | 155 | 106 | 105 | 101 | 621 | 124.2 |
| 0.0 | 1.0 | 104 | 82 | 87 | 92 | 73 | 438 | 87.6 |
| 0.1 | 1.0 | 66 | 125 | 88 | 60 | 79 | 424 | 84.8 |
| 1.0 | 1.0 | 141 | 114 | 132 | 11 | 127 | 633 | 126.6 |

Dissolving the Calcium Alginate Matrix and Plating the Protoplast-Derived Callus

Once protoplasts developed into callus colonies of approximately 16-32 cells within the alginate beads, we transferred the beads and conditioned feeder suspension into a 100×20 mm petri dish. Using forceps, we manually transferred individual beads to a 100×20 mm petri dish containing 40 ml of Lloyd and McCown minimal organics medium supplemented with 30 g/l sucrose, 10 mg/l Picloram and 2.0 mg/l TDZ. This transfer/washing process is repeated 2 additional times to eliminate any of the feeder suspension cells. We transferred washed beads into a 125 ml shake flask containing 20 ml of a 300 mM $KH_2PO_4$ solution. We pipetted the beads and solution up and down repeatedly through a 10 ml pipet up to ten time to break up the alginate matrix. We placed the flask on a gyratory shaker at 100 rpm sucrose, 10 mg/l Picloram and 2.0 mg/l TDZ.
Part 3: Stimulating Plant Regeneration from Protoplast Derived Mini Calli.

We prepared agar-solidified plates containing Pic/MT, Pic/TDZ and BN-Sorb and plated 0.5 ml of an actively growing grape suspension medium of various formulations on top of the agar, and covered the plated suspension with an 85 mm Whatman filter disk. We placed a 70 mm filter disc on top of the 85 cm filter and plated the solution containing the protoplast-derived colonies released from the calcium alginate matrix on top of the 7 cm disk creating a nurse over layer culture system. We have transferred intact calcium alginate beads containing protoplast-derived mini callus colonies to the top of the 70.0 mm filter paper and incubated them at 23 degrees centigrade in the dark.

LITERATURE CITED

Chee, R and R M Pool. 1987. Improved inorganic media constituents for in vitro shoot multiplication of *Vitis*. Sci. Hort. 32: 85.

Driver, J. A. and A. H. Kuniyuki. 1984. In vitro propagation of Paradox walnut rootstock. HortScience 19:507-509.

Gamborg O L, Miller R A, and K Ojima. 1968. Nutrient Requirements of suspension cultures of soybean root cells. Exp. Cell Research Vol. 50: 151-158.

Grosser, J. and Quitter F. 2011. Protoplast fusion for production of tetraploids and triploids: applications for scion and rootstock breeding in citrus. Plant Cell Tissue Organ Culture 104:343-357.

Lloyd, G and B H McCown. 1981. Commercially-feasible micropropagation of Mountain Laurel, *Kalmia latifolia*, by shoot tip culture. Proc. Int. Plant Prop. Soc. 30:421-427.

Murashige, T. and Skoog, F. 1962. A revised medium for rapid growth and bioassays with tobacco tissue cultures. Physiol. Plant. 15:473-497.

Nitsch, J P and C Nitsch. 1969. Haploid plants from pollen grains. Science 163: 85-87.

Quoirin, M. and P Lepoivre. 1977. Improved medium for in vitro culture of *Prunus* sp. Acta. Hort. 78:437-442.

Rugini, E. 1984. In vitro propagation of some olive (*Olea europaea* L.) cultivars with different root ability, and medium development using analytical data from developing shoots and embryos. Scientia Horticulturae 24: 123-134.

Schenk, R U and A C Hildebrandt. 1972. Medium and Techniques for Induction and Growth of Monocotyledonous and Dicotyledonous Plant Cell Cultures. Can. J. Bot. 50: 199-204.

Tricoli, D. M. Heins, M. B. Carnes M. G. 1986 Culture of Soybean mesophyll protoplasts in alginate beads. Plant Cell Reports 5:334-337.

Xu, X., Lu, J. Dalling, D., Jittayasothorn and Grosser, J. W. 2007. Isolation and Culture of Grape Protoplasts from Embryogenic Suspensions Cultures and Leaves of Vitus *vinifera* and *Vitis* rotuundifolia. Acta Hort. 738 pp 787-790.

Gamborg O L, Miller R A, and K Ojima. 1968, Chee, R and R M Pool. 1987, Driver, J. A. and A. H. Kuniyuki, 1984, Lloyd and McCown, 1981, Murashige, T. and Skoog, F., 1962, Quoirin, M. and P Lepoivre 1977, Rugini, E. 1984, and Schenk, R U and A C Hildebrandt, 1972.

Example 2. Regeneration of Whole Plants from Grape Protoplasts, a Basic Tool for Gene Editing The present example describes methods to, e.g., isolate plant protoplasts from embryogenic grape cells, generate mini callus colonies from the protoplasts, and regenerate embryos and plants from the callus.

Previous work with grape culture has disclosed methods for the establishment of suspension cultures, formation of somatic embryos from those cultures, and regeneration of whole plants from the somatic embryos. For example, somatic embryos derived from anther filaments can be transferred from agar-solidified plates to liquid WPM medium (Lloyd and McCown, 1981) supplemented with 20 g/liter sucrose, 1 g/liter casein hydrolysate, 10.0 mg/l Picloram, 2.0 mg/l metatopolin, 2 g/l activated charcoal, 100 mg/l ascorbic acid and 120 mg/l reduced glutathione (Pic/MTag), and grown in 125 ml shake flasks on a gyratory shaker at 90 rpms in the dark (FIG. 1).

When aliquots of these suspensions are transferred to agar solidified plates containing WPM medium (Lloyd and McCown, 1981) supplemented with 20 g/liter sucrose, 1 g/liter casein hydrolysate, 10.0 mg/l Picloram, 2.0 mg/l TDZ, 2 g/l activated charcoal, 100 mg/l ascorbic acid and 120 mg/l reduced glutathione (Pic/TDZ), highly embryogenic callus is produced (FIG. 2).

Either embryogenic callus from agar solidified plates or aliquots of suspension cultures can be used for the isolation of plant protoplasts.

Protoplast Isolation and Purification

Embryogenic callus of Merlot or Thompson Seedless were harvested from agar-solidified plates produced by plating cell suspensions onto Pic/TDZ medium. Cells were treated in an enzyme solution consisting of filter sterilized 0.5% Onozuka Cellulase R10, 0.25% pectinase, 0.25% macerozyme R10, 0.4 M mannitol, 5 mM $CaCl_2$, 10 g/l BSA, and 5 mM MES. Cells were subjected to infiltration under house vacuum for three, 2-minute exposures and the solution was incubated in the dark at 25 degrees centigrade on a platform shaker at 50 rpms. After approximately 16 hours incubation, the protoplast solution is filtered through a 40 μm screen and the protoplasts collected by pelleting via centrifugation at 2000 rpm for 10 minutes. The protoplasts were washed twice in an osmotically adjusted wash solution containing 0.4 M mannitol, 2 mM $CaCl_2$, 1 g/l BSA and 1,191 mg/l HEPES. Protoplasts derived from embryogenic callus harvested from agar solidified Pic/TDZ medium could be purified using a dextran gradient consisting of 2 ml of a 13% dextran solution, overlaid with 1.5 ml of 0.4 M wash medium. The protoplast band was readily harvested with a sterile Pasteur pipette, and transferred to a 60×15 mm petri dish. Yields of protoplasts from 500 mg fresh weight of embryogenic callus ranged from 2.5 to $8×10^6$ cells per ml (FIG. 3).

Generating Osmotically Adjusted Suspension Cultures

I have developed a method for encapsulating protoplasts in calcium alginate beads and culturing them in an osmotically conditioned feeder suspension culture. The feeder suspension is used to stimulate the protoplasts to divide to form calli even at low protoplast culture density. This is efficacious in soybean (Tricoli et al., 1986) and lettuce protoplasts. Protoplasts need to be cultured in high osmotic medium to prevent them from implosion or explosion prior to the reformation of their cell walls.

Osmotically conditioned grape feeder suspensions of Thompson Seedless and 1103P were generated by gradually increasing the osmotic potential of the suspension medium over time. During the bi-weekly subcultures of the suspension cultures, one-half of the suspension was removed and replaced with Pic/TDZ grape suspension medium containing 72.87 g/L mannitol, 1191 mg/l HEPES and 1 g/L BSA, pH 5.7. During the subsequent bi-weekly subculture, one-half of the old suspension was again removed and replaced with an equal volume of medium containing 72.87 g/L mannitol, 1191 mg/l HEPES and 1 g/L BSA, pH 5.7. This process was repeated biweekly so the cells could gradually acclimate to the high osmotic medium over time.

Encapsulating the Protoplasts

In order to generate the protoplast containing alginate beads, the protoplast density was adjusted to two times the desired final density with 0.4 M mannitol/buffer solution; generally $1×10^7$ protoplast per ml. The protoplast solution was mixed with an equal volume of a 6.4% or 3.2% sodium alginate solution (adjusted to pH 5.7). Beads were formed by drawing up the solution into a 12 ml sterile syringe and expelling the solution dropwise through a syringe needle into an osmotically adjusted 50 mM CaCl₂ solution. After 30 minutes in the CaCl₂ solution, the beads were rinsed one time in 0.4 M mannitol/buffer wash solution (FIG. 4). The size of the beads can be increased or decreased depending on the gauge of the needle. Either a 30.5 or 23-gauge needle was used to make beads that were approximately 2 mm or 5 mm in diameter, respectively. The gel strength of the beads was also modified by using either 6.4% or 3.2% sodium alginate. Varying both bead size and alginate concentration can affect the diffusion of nutrients into the beads.

In addition to allowing one to test various media formulations, embedding protoplasts in calcium alginate beads also ensures that each protoplast-derived callus colony is of single cell descent. This is important for gene editing experiments, since if protoplasts are not fixed in a matrix they will rapidly clump together, making determination of single cell descent impossible. Normally when cultured at low density, protoplasts fail to divide. However, culturing embedded protoplasts in conditioned medium or with feeder suspensions has been shown to stimulate protoplast division in other species, even at very low cell densities. Since the alginate matrix is permeable to nutrients, the conditioned medium serves as a nurse culture for the low-density cultured protoplasts. Previously, I have demonstrated that a single protoplast encapsulated in a 2-5 mm alginate bead could be stimulated to divide using this nurse culture system for both soybean and lettuce.

Development of Mini-Calli from Encapsulated Protoplasts Using Feeder Suspensions Using feeder cell suspension, I have been able to stimulate isolated grape protoplasts to divide and form callus. The use of a feeder suspension greatly improved cells division and callus colony formation from protoplasts when compared to conditioned medium alone. Embedded protoplasts were resuspended in conditioned osmotically adjusted grape cell suspension cultures in 125 ml shake flasks and incubated at

26

Figure 9:
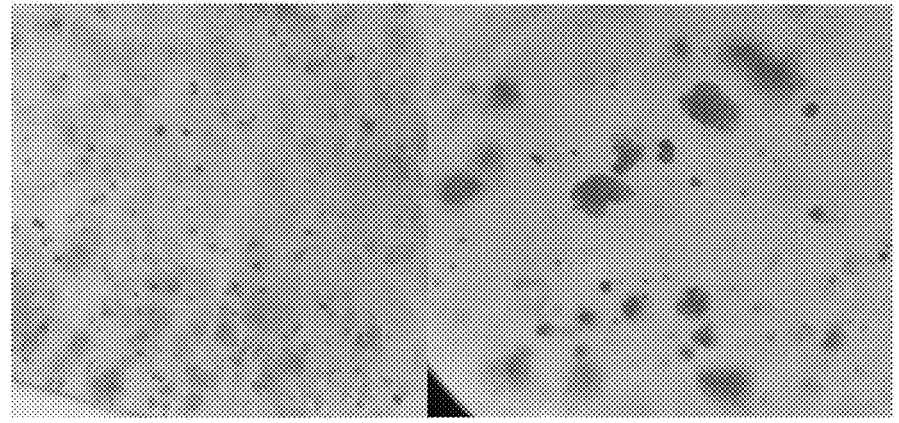
FIG. 9. Callus formation from encapsulated Thompson seedless protoplasts cultured in grape feeder suspension medium with 1× antioxidant mixture (left) and 5× antioxidant mixture (right).

Callus colonies that develop in alginate beads often became discolored due to phenolic production. I have developed and tested an antioxidant solution consisting of 100 mg/l ascorbic acid, 150 mg/l citric acid, 30 mg/l reduced glutathione and 100 mg/l L-cysteine (PTF AQ). I tested the effect of this antioxidant addendum on protoplast viability and division on Thompson seedless and Merlot protoplast culture. Protoplast were isolated and encapsulated in 1.6% calcium alginate beads. Calcium alginate beads from the same protoplast preparation were randomly transferred to shake flasks containing conditioned 0.4 M Pic/TDZ 1103P feeder cell suspensions with or without the addition of 1× or 5× of the antioxidant solutions. After 14 days, the osmotic strength of the feeder suspension was reduced from 0.4 M to 0.2 M mannitol. At day 35, I randomly harvested five beads per treatment and counted the number of mini calli per bead. For both Merlot and Thompson seedless protoplasts, a significantly higher percentage of callus colonies were observed developing in beads grown in the suspensions containing the antioxidant solution (Table 1). Merlot protoplasts tend to produce more phenolic than Thompson seedless protoplasts and the antioxidant addendum had a much more profound effect on the division of the Merlot protoplasts than the Thompson seedless protoplasts. Without the addition of the antioxidant mixture, no mini calli were observed after 35 days in culture, whereas an average of 168 mini calli were produced per bead from protoplasts grown in feeder cultures with the antioxidant addendum (Table 1). I also observed increased Thompson seedless and Merlot protoplast viability and increased callus development with increasing antioxidant concentrations (Table 2; FIG. 9). Lastly, the addition of the polyamine spermine (SPM) significantly enhanced the number and speed of mini-callus formation from both Thompson seedless and Merlot derived protoplasts (Table 4, Table 5).

Callus colonies continued to develop within the calcium alginate beads and often grow large enough that they could be seen rupturing through the surface of the beads (FIG. 6).

TABLE 5

Average number of Merlot callus colonies per bead when cultures in 1103P cell feeder suspension supplemented with 1.0 mM PUT, 0.1 mM SPD, and 0.0 to 1.0 mM SPM
Number of colonies per bead

| | SPM | | | | | |
|---|---|---|---|---|---|---|
| | 0.0 mM | 0.1 mM | 0.25 mM | 0.5 mM | 0.75 mM | 1.0 mM |
| Bead | | | | | | |
| 1 | 0 | 0 | 0 | 0 | 0 | 7 |
| 2 | 0 | 1 | 0 | 0 | 0 | 9 |
| 3 | 0 | 0 | 0 | 0 | 0 | 5 |
| 4 | 0 | 0 | 0 | 0 | 0 | 6 |
| 5 | 0 | 0 | 0 | 1 | 0 | 4 |
| Total | 0 | 1 | 0 | 1 | 0 | 31 |
| Ave 3 colonies per bead | 0 | 0.2 | 0 | 0.2 | 0 | 6.2 |

100 rpm and 25 degrees centigrade. Viable protoplasts began dividing within 7 days. An equal volume of grape suspension culture medium without mannitol was added to the flasks at day 14, thereby reducing the starting mannitol concentration to 0.2 M. After 14 additional days, an equal volume of grape suspension culture medium without mannitol was again added to the flasks, thereby reducing the starting mannitol concentration to 0.1 M. By day 21 post encapsulating, small callus colonies were visible (FIG. 5).

Once protoplasts developed into callus colonies of approximately 16-32 cells within the alginate beads (approximately 12 weeks), I transferred the beads and conditioned feeder suspension into a 100×20 mm petri dish. Using forceps, I manually transferred individual beads to a 100×20 mm petri dish containing 40 ml of Lloyd and McCown minimal organics medium supplemented with 30 g/l sucrose, 10 mg/l Picloram and 2.0 mg/l TDZ. This transfer/washing process was repeated 1-2 more times to eliminate

US 12,593,767 B2

Figure 10:
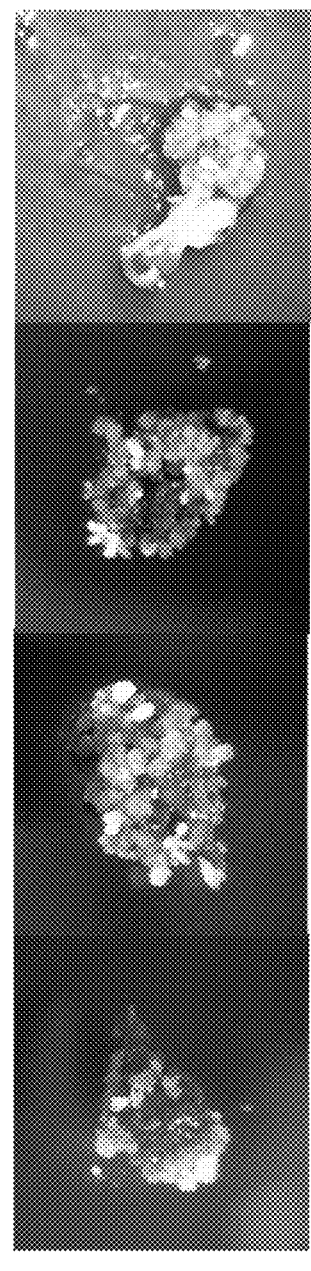
FIG. 10. Somatic embryos developing from protoplast derived callus encapsulated in calcium alginate beads.

27 any of the feeder suspension cells. Beads were then transferred onto feeder agar-solidified 100×20 mm petri dish containing 40 ml of Lloyd and McCown minimal organics medium supplemented with 30 g/l sucrose, 10 mg/l Picloram and 2.0 mg/l TDZ onto which 1.0 ml of a 1103P grape cell suspension was plated. An 85 mm Whatman filter paper was placed over the plated suspension and a 70 mm Whatman filter paper placed on top of the 85 mm filter. Beads were placed on top of the 70 mm filter paper. One ml Lloyd and McCown minimal organics medium supplemented with 30 g/l sucrose, 10 mg/l Picloram and 2.0 mg/l TDZ was added to each plate in prevent desiccation. After approximately four weeks, individual beads were then transferred to agar solidified WPM supplemented with 20 g/l sucrose, 1 g/l casein, 1 mM MES, 500 mg/l activated charcoal, 0.5 mg/l BAP, 0.1 mg/l NAA 50 g/l sorbitol and 14 g/l agar and mini-calli developed somatic embryos (FIG. 10). Embryos failed to develop on other media tested.

Figure 11:
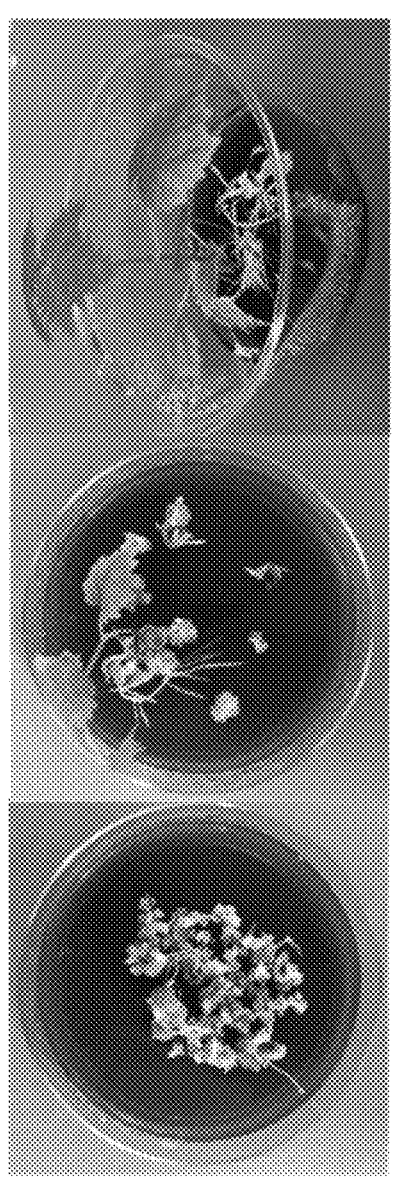
FIG. 11. Thompson seedless grape embryos and plants developing from protoplast derived callus encapsulated in calcium alginate beads from experiment 18355.

Once embryos were formed, the beads were transferred to agar solidified WPM supplemented with 20 g/l sucrose, 1 g/l casein, 1 mM MES, 500 mg/l activated charcoal, 0.5 mg/l BAP, 0.1 mg/l NAA 0.0 g/l sorbitol and 7 g/l agar, which induced germination of the developing somatic embryos and production of plants (FIG. 11).

Figure 12:
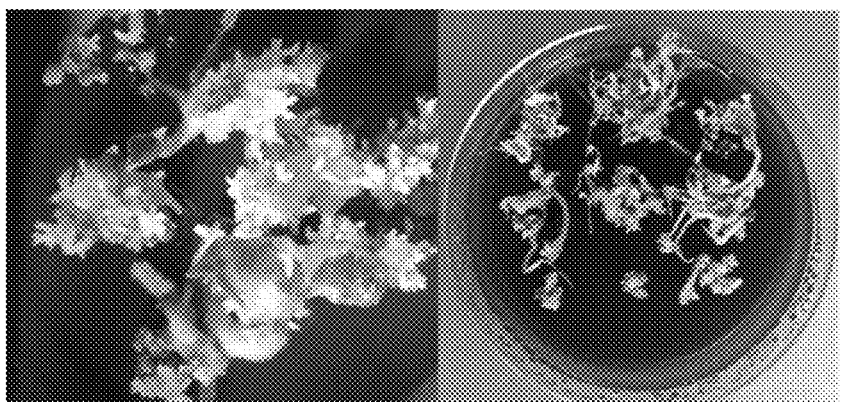
FIG. 12. Thompson seedless grape embryos developing from protoplast derived callus encapsulated in calcium alginate beads from experiment 19129.

These results have now been replicated three times using Thompson Seedless grapes (FIG. 12).

Figure 13:
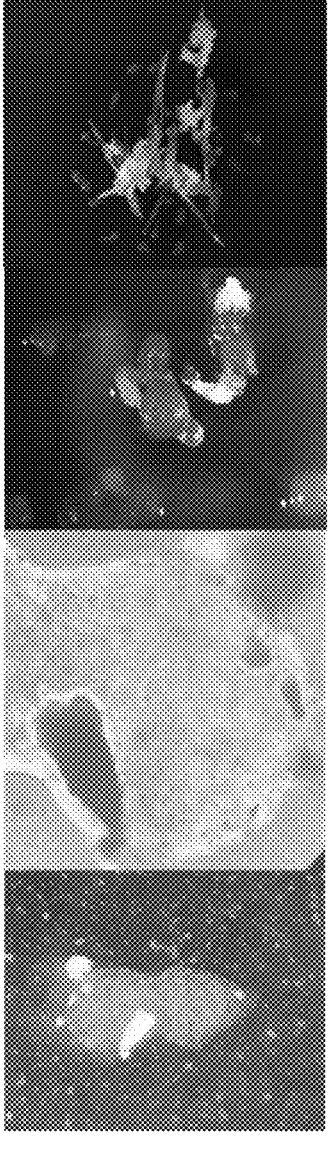
FIG. 13. Merlot embryos developing from encapsulated protoplast within a calcium alginate bead and subsequent germination of embryos.
Figure 14:
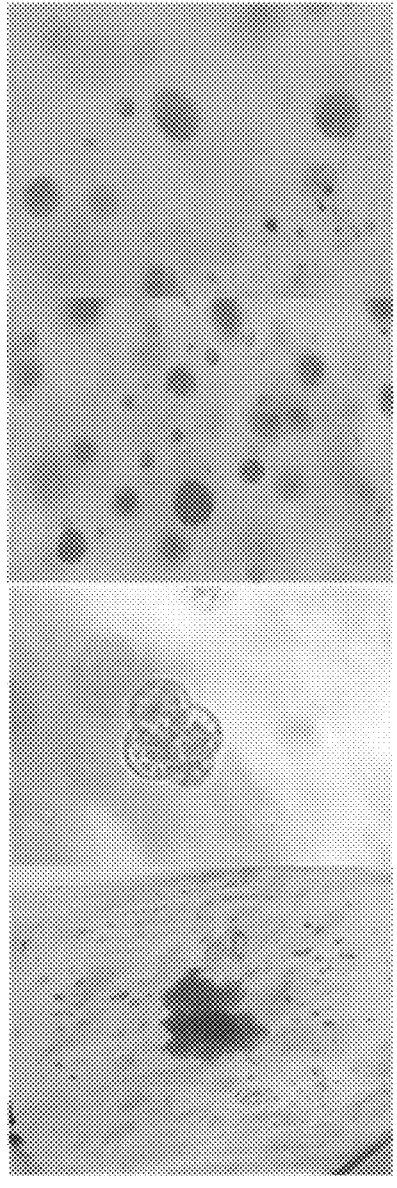
FIG. 14. Early cell division and colony formation from protoplasts encapsulated in calcium alginate beads. From left to right, Chardonnay, 101-14, Merlot and Thompson seedless.

This procedure has recently been repeated for the wine genotype, Merlot. Although regeneration frequencies were much lower than for Thompson Seedless, we are seeing embryos develop from isolated protoplasts (FIG. 13).

REFERENCES

Wang et al., 2015 An efficient PEG-mediated transient gene expression system in grape protoplasts and its application in subcellular localization studies of flavonoids biosynthesis enzymes. Scientia Horticulturae 191 (2015) 82-89.

Xu, X., Lu, J. Dalling, D., Jittayasothorn and Grosser, J. W. 2007. Isolation and Culture of Grape Protoplasts from Embryogeneic Suspensions Cultures and Leaves of Vitus *vinifera* and *Vitis* rotuundifolia. Acta Hort. 738 pp 787-790.

Zhu et al., 1997. Highly efficient system of plant regeneration from protoplasts of grapevine (*Vitis vinifera* L.) through somatic embryogenesis by using embryogenic callus culture and activated charcoal Plant Science 123 (1997) 151 157.

Example 3. Additional Findings

In addition to Thompson Seedless and Merlot grapes, we have now successfully embedded protoplasts and regenerated callus colonies from the wine grape, Chardonnay and grape rootstock genotype 101-14.

We have now found that we can regenerate plants from encapsulated grape protoplasts without dissolving the alginate matrix. Once protoplasts developed into callus colonies of approximately 16 to 32 cells within the alginate beads (approximately day 40 to 50), we transfer the beads and conditioned feeder suspension into a 100×20 mm petri dish. Using forceps, we manually transferred individual beads to a 100×20 mm petri dish containing 40 ml of Lloyd and McCown minimal organics medium supplemented with 20 g/l sucrose, 1 g/l casein, 222 mg/l CaCl₂, without hormones or activated charcoal. We repeated this transfer/washing process two more times to eliminate any of the feeder suspension cells. We then transferred beads onto

Figure 15:
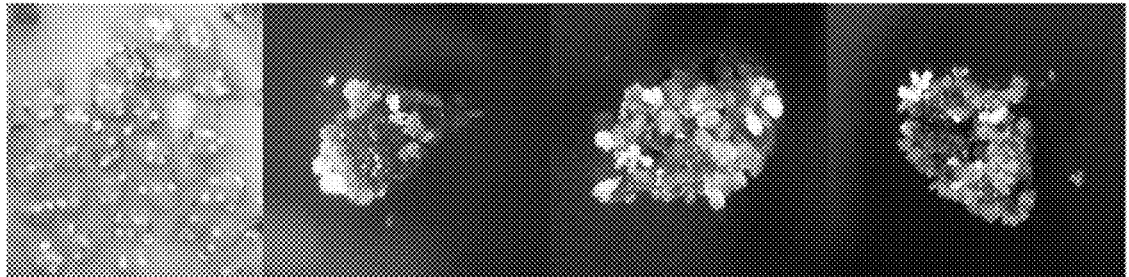
FIG. 15. Somatic embryos developing from protoplast-derived callus encapsulated in calcium alginate beads.

28 agar-solidified 100×20 mm feeder plates containing 40 ml of Lloyd and McCown minimal organics medium supplemented with 20 g/l sucrose, 50 g/l sorbitol, 1 g/l casein, 1 mM MES, 0.5 mg/l BAP and 0.1 mg/l NAA onto which 1.0 ml of a 1103P grape suspension culture is plated. The grape suspension culture medium consisted of WPM medium supplemented with 20 g/l sucrose 10 mg/l picloram and 2.0 mg/l TDZ, 72.87 g/L mannitol, 222 mg/l CaCl₂, 1 g/l casein, 1,191 mg/l HEPES and 2 g/l activated charcoal, pH 5.7. We placed an 85 mm Whatman filter paper over the plated suspension and a 70 mm Whatman filter paper on top of the 85 mm filter. We placed beads on top of the 70 mm filter paper. We add 1 ml Lloyd and McCown minimal organics medium supplemented with 30 g/l sucrose, 1 g/l casein, 1 mM MES, 10 mg/l picloram and 2.0 mg/l TDZ to each plate to prevent desiccation. We incubated the cultures at 26 degrees centigrade in the dark. After approximately 3-4 weeks, mini-calli developed into somatic embryos within the beads (FIG. 15).

Figure 16:
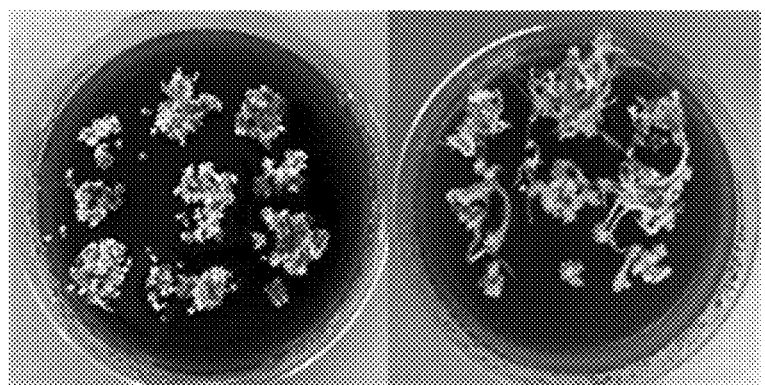
FIG. 16. Somatic embryos developing from protoplast-derived callus encapsulated in calcium alginate beads and maintained on high sorbitol containing medium remain dormant (left) until transferred to medium without sorbitol (right).
Figure 17:
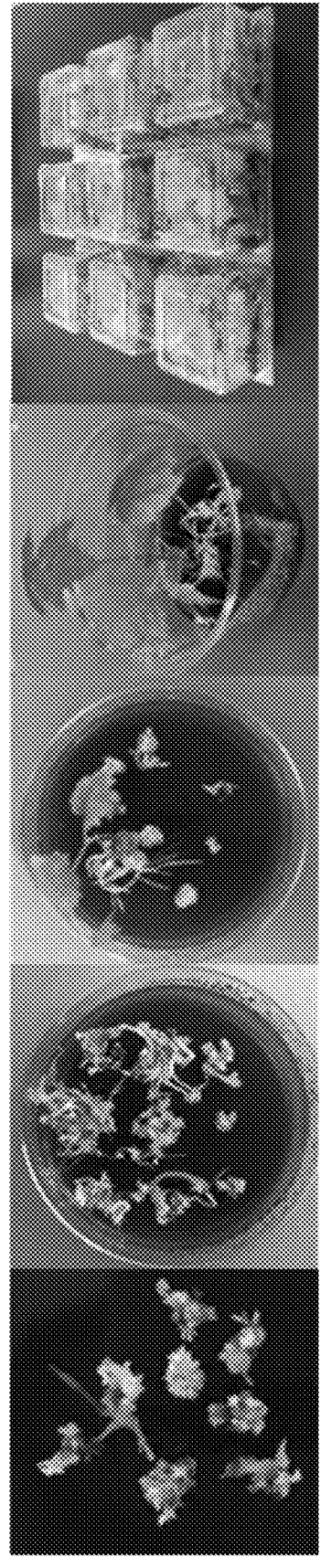
FIG. 17. Thompson seedless grape embryos and plants produced from protoplasts encapsulated in calcium alginate beads and transferred to medium lacking sorbitol.

If we maintain the beads on agar-solidified medium containing sorbitol, the embryos will not germinate further and become dormant (FIG. 16). This can be valuable since it allows one to store embryos from gene editing studies, which can be germinated as needed for genetic analysis. We are able to stimulate germination and plant production from the protoplast-derived dormant somatic embryos by transferring the embryo containing alginate beads to medium lacking sorbitol on which they germinate and develop into whole plants (FIGS. 16, 17).

Figure 18:
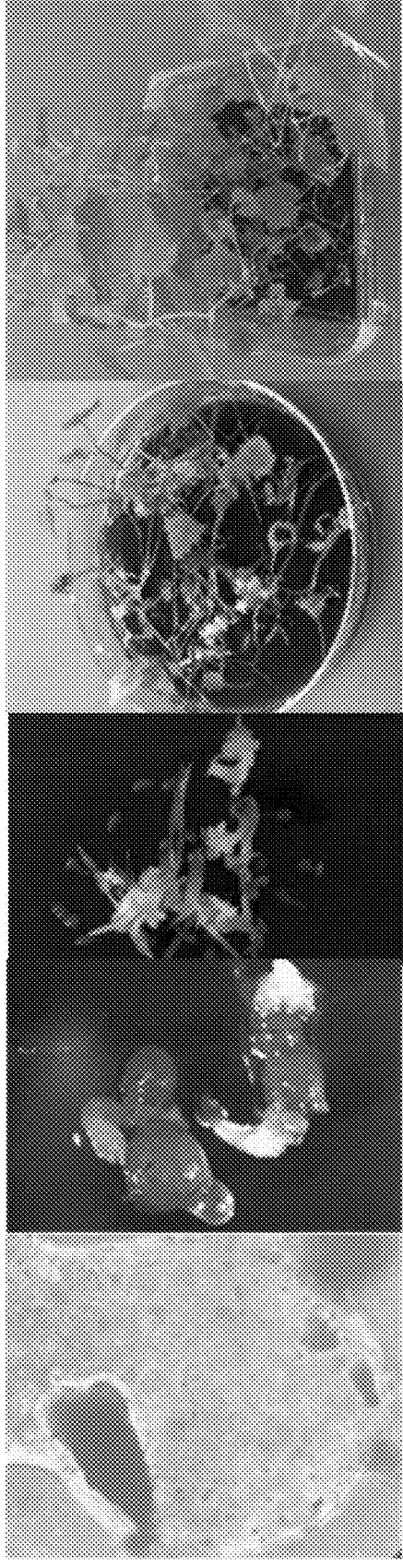
FIG. 18. From left to right: Merlot embryos developing from encapsulated protoplasts within a calcium alginate bead, embryos emerging out of calcium alginate beads, embryos germinating on solidified medium, elongating rooted protoplast-derived plants and rooted plants in culture.

We have repeated this procedure for the wine genotype, Merlot. Although regeneration frequencies were lower than for Thompson Seedless, we have been able to regenerate whole plants from encapsulated Merlot protoplasts (FIG. 18).

Figure 19:
FIG. 19. Thompson Seedless (green stakes, on left) and Merlot (purple stakes, on right) plants derived from protoplast culture.

We have successfully acclimated protoplast derived plants of both Merlot and Thompson Seedless to soil and they appear phenotypically normal (FIG. 19).

Protoplast Transfection

Figure 20:
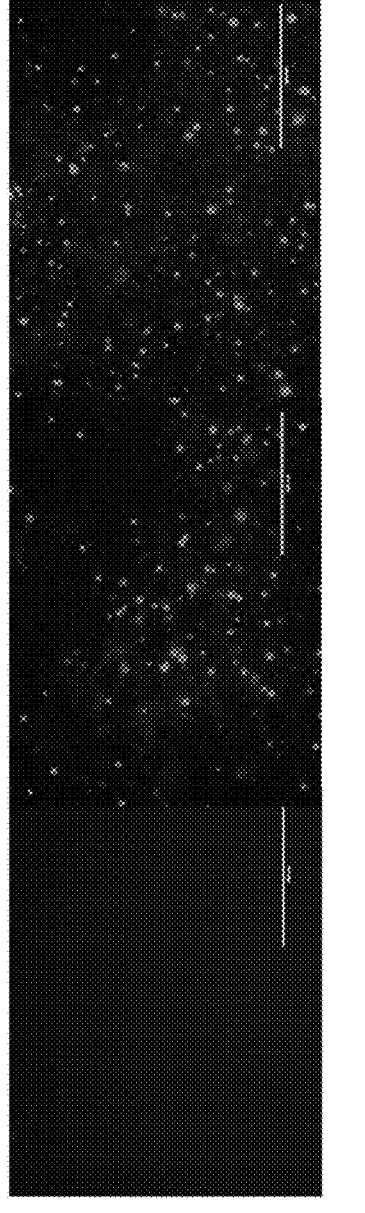
FIG. 20. Expression of mCherry in Thompson Seedless protoplasts 72 hours after transfection (left to right 0, 10 and 20 µg plasmid DNA).
Figure 21:
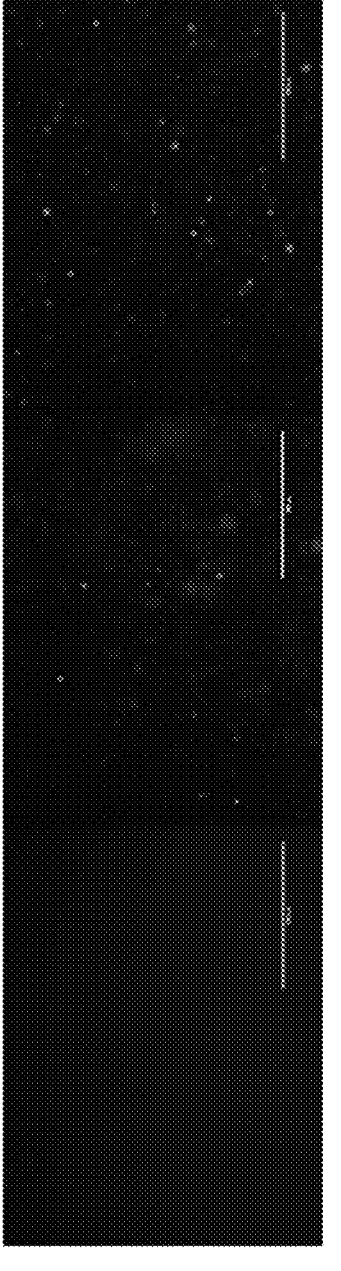
FIG. 21. Expression of mCherry in 101-14 protoplasts 72 hours after transfection (left to right 0, 10, and 20 µg plasmid DNA).

We harvest embryogenic callus of the table grape cultivar, Thompson Seedless and the rootstock genotype 101-14 from agar-solidified plates containing Pic/TDZ medium. We treated cells in an enzyme solution consisted of filter sterilized 0.5% Onozuka Cellulase R10, 0.25% pectinase, 0.25% macerozyme R10, 0.4-0.6 M mannitol, 5 mM CaCl₂, 10 g/l BSA, and 5 mM MES. We subjected the cells to infiltration under house vacuum for three, 2-minute exposures and incubated the solution in the dark at 25 degrees centigrade on a platform shaker at 50 rpms. After approximately 16 hours incubation, we filtered the protoplast solution through a 40 um screen and collected the protoplasts by pelleting via centrifugation at 700×g for 10 minutes. We washed the protoplasts twice in an osmotically adjusted wash solution containing 0.4 M mannitol, 2 mM CaCl₂, 1 g/l BSA and 1,191 mg/l HEPES. We purify protoplasts derived from embryogenic callus harvested from agar solidified Pic/TDZ medium using a dextran gradient consisting of 2 ml of a 13% dextran solution, overlaid with 1.5 ml of 0.4 M wash solution. We collected the protoplast band with a Pasteur pipette and transferred them to a 15 ml centrifuge tube and pelleted at 700×g for 10 minutes. We removed the supernatant and re-suspended the protoplast in W5 solution at a density to 3.0×10⁶ per ml. We transferred 100-200 μl of the protoplasts suspension into 2.0 ml tubes and pelleted at 700×g for 10 minutes. We removed the supernatant and added 0, 10 or 20 ug of mCherry plasmid DNA to the pelleted protoplasts using a gentle swirling motion to mix the DNA with the protoplast. Next, we added 100 to 200 μl of a freshly prepared PEG solution again using a gentle swirling motion. Lastly, we added an equal volume of a MMG solution and gently inverted the tube to mix. We incubated the protoplast at room temperature in the dark for 15 to 20 minutes. After 20 minutes we added 880 μl of W5 solution to the tubes to stop the transfection, transfer to a 15 ml centrifuge tube and pellet at 700×g for 10 minutes. We then wash the pellet in 4 ml W5 solution, pellet and re-suspend in 1 ml W1 solution and transfer to 24 well plate. We incubate the protoplasts in the dark at room temperature and agitate at 40 rpms. After 72 hours observe under fluorescence for transfected protoplasts using a Life Technology EVOS inverted fluorescent microscope (FIGS. 20, 21).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of regenerating a grape plant from a grape protoplast, the method comprising:
   (i) encapsulating an isolated grape protoplast in a gel matrix;
   (ii) culturing the encapsulated protoplast in the presence of an osmotically conditioned grape cell suspension culture, wherein the osmotically conditioned grape cell suspension culture is supplemented with picloram and thidiazuron and wherein the protoplast undergoes cell division;
   (iii) culturing the encapsulated protoplast in the presence of activated charcoal and one or more antioxidants and polyamines, wherein the protoplast undergoes cell division and forms a callus colony;
   (iv) transferring the callus colony to an agar-solidified feeder medium, wherein the callus colony develops into a somatic embryo; and
   (v) transferring the somatic embryo to an agar-solidified plant medium, wherein the somatic embryo undergoes germination.

2. The method of claim 1, wherein the gel matrix is an alginate bead.

3. The method of claim 1, wherein the one or more antioxidants are selected from the group consisting of ascorbic acid, citric acid, reduced glutathione, and L-cysteine.

4. The method of claim 1, wherein the one or more antioxidants comprise ascorbic acid, citric acid, reduced glutathione, and L-cysteine.

5. The method of claim 1, wherein the polyamine is spermine.

6. The method of claim 1, wherein the encapsulated protoplast is cultured in step (iii) in a feeder cell suspension.

7. The method of claim 2, further comprising a step in which the alginate bead formed in step (i) is dissolved prior to the transferring of step (v).

8. The method of claim 2, wherein the alginate bead formed in step (i) is not dissolved prior to the transferring of step (v).

9. The method of claim 1, further comprising a step in which the protoplast is isolated from an embryonic callus or somatic embryo prior to step (i).

10. The method of claim 9, wherein the embryonic callus or somatic embryo from which the protoplast is isolated is derived from an anther filament.

11. The method of claim 9, wherein the protoplast is isolated from an embryonic callus or somatic embryo culture.

12. The method of claim 11, wherein the embryonic callus or somatic embryo culture is produced by generating a suspension culture from an anther-derived callus and plating aliquots of the suspension culture onto callus or somatic embryo induction medium.

13. The method of claim 1, further comprising a step in which a guide RNA and an RNA-guided nuclease are introduced into the isolated protoplast prior to the encapsulating of step (i).

14. The method of claim 13, wherein the RNA-guided nuclease is a Cas protein.

15. The method of claim 13, wherein the guide RNA and RNA-guided nuclease are introduced into the protoplast using PEG or electroporation.

16. The method of claim 13, wherein the guide RNA and RNA-guided nuclease are introduced into the protoplast as a ribonucleoprotein (RNP).

17. The method of claim 16, wherein the guide RNA and the RNA-guided nuclease are transiently expressed in the protoplast.

18. The method of claim 13, wherein the guide RNA and RNA-guided nuclease induce an alteration in the protoplast genome.

19. The method of claim 1, further comprising a step wherein the somatic embryo developed in step (iv) is stored indefinitely on a sorbitol-containing medium prior to the transferring to the plant medium of step (v), wherein the plant medium does not comprise sorbitol.

* * * * *